(12) United States Patent
Guertin

(10) Patent No.: US 8,012,481 B2
(45) Date of Patent: Sep. 6, 2011

(54) COMPOSITION AND METHOD FOR INDUCING OR RESTORING LOCOMOTOR FUNCTIONS IN AN ANIMAL

(75) Inventor: Pierre Guertin, Quebec (CA)

(73) Assignee: Universite Laval (CA)

(*) Notice: Subject to any disclaimer, the term of this patent is extended or adjusted under 35 U.S.C. 154(b) by 933 days.

(21) Appl. No.: 11/662,100

(22) PCT Filed: Sep. 1, 2005

(86) PCT No.: PCT/CA2005/001337
§ 371 (c)(1),
(2), (4) Date: Nov. 20, 2007

(87) PCT Pub. No.: WO2006/026850
PCT Pub. Date: Mar. 16, 2006

(65) Prior Publication Data
US 2008/0096847 A1    Apr. 24, 2008

Related U.S. Application Data

(60) Provisional application No. 60/607,256, filed on Sep. 7, 2004.

(51) Int. Cl.
*A61K 38/22* (2006.01)
(52) U.S. Cl. .................. 424/143.1; 424/1.45; 530/388.4
(58) Field of Classification Search .................. None
See application file for complete search history.

(56) References Cited

U.S. PATENT DOCUMENTS
2004/0235913 A1    11/2004 Cuny et al.

FOREIGN PATENT DOCUMENTS
CA    2 422 055 A1    3/2002
CA    2 397 371 A1    2/2003

OTHER PUBLICATIONS

Barbeau, 1991, Brain Research, 546, 250-260.*
O'Neill, 2000, European Journal of Pharmacology, 399, 49-55.*
Shimazu, 2001, European Journal of Pharmacology, 421, 181-189.*
[Retrieved from]:http://www.aurorahealthcare.org/yourhealth/healthgate/getcontent.asp?URLhealthgate=11662.html, 4 pages, 2010 [Retrieved on Oct. 1, 2010].*
[Retrieved from]: http://www.mayoclinic.com/health/spinal-cord-injury/DS00460/DSECTION=treatments-and-drugs, 3 pages [Retrieved on Sep. 20, 2010].*
[Retrieved from]: http://www.healthscout.com/ency/68/53/main.html, 3 pp. [Retrieved on 10/1/10].*
McEwen, 1997, Behavioral Neuroscience, 111, 825-833.*
Queiroz, 1997, Life Sciences, 61, 371-382.*
Rossignol, 1998, Annals New York Academy of Sciences, 860, 346-359.*
De Mello 2004, Spinal cord, 42, 218-212.*
Guertin Pierre A., "Synergistic activation of the central pattern generator for locomotion by L-beta-3,4-dihydroxyphenylalanine and quipazine in adult paraplegic mice", Neuroscience Letters, 2004, vol. 358, No. 2, pp. 71-74.
Shimazu Seiichiro et al., "(−)-1-(Benzofuran-2-yl)-2-propylaminopentane enhances locomotor activity in rats due to its ability to induce dopamine release", European Journal of Pharmacology, 2001, vol. 421, No. 3, pp. 181-189.
Rossignol S. et al., "Pharmacological Activation and Modulation of the Central Pattern Generator for Locomotion in the Cat", Annals New York Academy of Sciences, 1998, vol. 860, pp. 346-359.
Barbeau H., et al., "Initiation and modulation of the locomotor pattern in the adult chronic spinal cat by noradrenergic, serotonergic and dopaminergic drugs", Brain Research, 1991, vol. 546, pp. 250-260.
McEwen Melanie L., et al., "L-DOPA and Quipazine Elicit Air-Stepping in Neonatal Rats With Spinal cord Transections", Behavioral Neuroscience, 1997, vol. 111, No. 4, pp. 825-833.
Madriaga M.A., et al., "Modulation of Locomotor Activity by Multiple 5-HT and Dopaminergic Receptor Subtypes in the Neonatal Mouse Spinal Cord", J. Neurophysiol., 2004, vol. 92, No. 3, pp. 1566-1576.
O'Neill Michael F., et al., "5-$HT_{IB/D}$ receptor agonist, SKF99101H, induces locomotor hyperactivity in the guinea pig", European Journal of Pharmacology, 2000, vol. 399, pp. 49-55.
Bregman Barbara S., et al., "Recovery from spinal cord injury mediated by antibodies to neurite growth inhibitors", Nature, 1995, vol. 378, pp. 498-501.
Chen Henrich, et al., "Spinal Cord Repair in Adult Paraplegic Rats: Partial Restoration of Hind Limb Function", Science, 1996, vol. 273, pp. 510-513.
Borgens, Richard B., et al., "Enhanced Spinal Cord Regeneration in Lamprey by Applied Electric Fields", Science, 1981, vol. 213, pp. 611-617.
Basso, Michele D., et al., "Graded Histological and Locomotor Outcomes after Spinal Cord Contusion Using the NYU Weight-Drop Device versus Transection", Experimental Neurology, 1996, vol. 139, pp. 244-256.
Antri M., et al., "Locomotor recovery in the chronic spinal rat: effects of long-term treatment with a 5-$HT_2$ agonist", European Journal of Neuroscience, 2002, vol. 16, pp. 467-476.
Guertin, Pierre A., "Role of NMDA receptor activation in serotonin agonist-induced air-stepping in paraplegic mice", Spinal Cord, 2004, pp. 1-6.
Guertin, Pierre A., "Synergistic activation of the central pattern generator for locomotion by L-beta-3,4-dihydroxyphenylalanine and quipazine in adult paraplegic mice", Neuroscience Letters, 2004, pp. 1-4.

* cited by examiner

*Primary Examiner* — Cecilia Tsang
*Assistant Examiner* — Satyanarayana Gudibande
(74) *Attorney, Agent, or Firm* — Baker & Hostetler LLP

(57) ABSTRACT

The present invention relates to the field of neuropathological disorders involving impaired locomotor functions. More specifically, the present invention relates to a composition and method for inducing and restoring locomotor functions, such as basic walking movements in the lower extremities of chronic spinal cord injured animals, such as paraplegic or tetraplegic individuals.

11 Claims, 25 Drawing Sheets

| | buspirone (6-8 mg/kg, n=7) | buspirone (2-4 mg/kg, n=5) |
|---|---|---|
| NLM | 8.2 ± 3.6 | 5.2 ± 4.0 |
| LM | 10.2 ± 4.0 | 0.8 ± 0.2 |
| Incidence NLM | 5/7 (71%) | 3/5 (60%) |
| Incidence LM | 5/7 (71%) | 3/5 (60%) |
| Mov. Amplitude | 1.6 ± 0.4 | 0.8 ± 0.4 |

FIG. 17

COMPOSITION AND METHOD FOR INDUCING OR RESTORING LOCOMOTOR FUNCTIONS IN AN ANIMAL

CROSS REFERENCE TO RELATED APPLICATIONS

This application is a National Stage of, and claims priority to Patent Cooperation Treaty (PCT) Application No. PCT/CA2005/001337 filed on Sep. 1, 2005, which claims priority to U.S. Provisional Application No. 60/607,256, filed Sep. 7, 2004, all of the above disclosures are herein incorporated by reference in their entirety.

FIELD OF THE INVENTION

The present invention relates to the field of neuropathological disorders involving impaired locomotor functions. More specifically, the present invention relates to a composition and method for inducing and restoring locomotor functions, such as basic walking movements in the lower extremities of chronic spinal cord injured animals.

DESCRIPTION OF THE PRIOR ART

Body functions such as locomotion, muscle reactions, coordination, and several of other physiological aspects are tightly dependent of the spinal cord integrity. Human locomotor activities such as walking, jogging and running, involves the largest muscles and bones in the body, and must be supported by the cardiovascular, respiratory, metabolic and nervous systems. This activity normally determines the capacity or condition, not only of the leg and backbones and muscles, but also of the heart, lungs and influences the amount of fat in the body and bloodstream. Knowledge of human locomotor activity is essential to both research and clinical practice in such diverse areas as physical conditioning, weight control, prevention of osteoporosis, cardio respiratory conditions, and the maintenance of condition of individuals in space flight.

The mammalian spinal cord shows little spontaneous recovery after injury. Furthermore, although regeneration of damaged spinal cord tissues (e.g., axons and neurons) can sometimes be induced through treatment, the treated animals still do not usually recover whatever voluntary motor function was lost to the injury.

The degree of motor function loss varies with the identity of the damaged tissue and the extent of damage incurred, as well as with species. For example, the rubrospinal tract influences movement through direct and reciprocal spinal motor projections that reflect activity of the rubro-cortico-cerebellar premotor pathway. The vestibulospinal and reticulospinal tracts affect postural control and balance during locomotion. Specialization in the vestibular system in particular has been important for the evolution of bipedal locomotion in humans. However, impairments in voluntary motor function after spinal cord injury in humans are most often attributed to disruption of corticospinal tract (CST) projections.

In rodents, a family frequently used to study spinal cord regeneration, CST lesions have been reported to impair skilled motor movements, such as reaching, preferred limb use, and "placing" responses (reflex limb withdrawal to touch). Studies in cats and non-human primates report that the CST is involved in voluntary modification of gait, inducing alterations in amplitude, duration and temporal patterns of muscle activity during locomotion through both direct projections to motor neurons and through modification of activity of spinal cord pattern generators. In humans, some voluntary motor function can occasionally be recovered spontaneously despite isolated lesions of the CST, although function is generally inferior to the pre-lesioned state.

Two reports of partial functional recovery resulting from regrowth of host projections after spinal cord injury have recently been published. In one approach, CNS myelin-associated growth inhibitors were neutralized (Bregman B S, Kunkel-Bagden E, Schnell L, Dai H N, Gao D, Schwab M E (1995) Nature 378:498-501), resulting in regrowth of axons through host white matter. In a second study, delivery of acidic fibroblast growth factor reportedly generated growth responses from all supraspinal systems studied, resulting in some functional recovery after complete spinal cord transections (Cheng H, Yihai C, Olson L. (1996) Science 273:510-513). Regenerating axons in the latter experiment were specifically directed toward host gray matter to avoid myelin-based inhibitors. These findings highlight the importance of defining appropriate growth terrains for injured adult CNS axons and of identifying specific growth-promoting neurotrophic factors.

The spinal cord plays a critical role in the functioning of the central nervous system (CNS). Although the spinal cord is the simplest region of the CNS, it contains diverse neural cell types which are interconnected in intricate patterns. During embryonic development, multi-potent stem cells in the neural tube proliferate and then ultimately differentiate into neurons and glia according to extrinsic cues and intrinsic determinants. Diseases and injuries that affect the functioning of spinal cord neural cells are often debilitating, and generally remain difficult to treat effectively.

Spinal cord injury is a devastating injury with, today, no significantly useful therapy. Emergency medical treatment for spinal-cord injury patients has included prompt triage and intensive rehabilitation. These therapies have somewhat increased or optimized remaining neurologic functions in those patients and prevented further injury to the spinal cord. However, only a minority of patients ever achieve any major neurologic recovery. As a result, no effective acute treatment or rehabilitation therapy is presently available for the approximately 10,000 new patients per year which suffer from major spinal cord injury and the consequent permanent disability. There is today approximately 500,000 chronic spinal cord injured individuals in North America and Europe only.

The spinal cord injury has often been seen in athletes' injury and victims of car accidents. Since the patients are sometimes paralyzed and require a life-long care, a method of enhancing the motor recovery has been strongly desired. While biochemical and molecular biological approaches have been vigorously tried, but a study to find physical means to enhance the motor function recovery has been delayed.

The effect that completely severed spinal cord of a lamprey was regenerated in 2 months by application of 10 mA of DC current across the severed section has been reported earlier (Borgens, R. B. et al., "Science", 1981, Vol. 213, pages 611-617). They described that the electric current had a direct effect on the nerve regeneration, but the molecular mechanism has not been elucidated. However, in contrast to all mammalian species, lampreys and other types of ancient vertebrates (e.g., fish, amphibians and reptiles) have some demonstrated capacity to regenerate their peripheral and central nervous system including the spinal cord. Therefore, these results with electrical stimulation, although interesting, have unfortunately no direct application for the design of future therapeutic approaches dedicated to spinal cord injured mammals.

By using electric stimulating devices, influence(s) of the static electricity to a living body through tests using experimental animals have been studied to seek a new applicable use(s) of it. As a result, it has been found that the device is useful for inhibiting a decrease in an amount of bone to prevent and cure osteoporosis and also inhibiting an appetite without increasing a body weight to prevent and cure obesity. The related patent application was filed in Japan in the name of assignee company [Japanese Patent 9-322944(A) which corresponds to U.S. Pat. No. 5,836,997]. However, this approach needs again heavy equipment and protocols to induce regular effects and is not easy to use or even accessible for most patients suffering of spinal cord injuries.

The importance of at least partially restoring locomotor functions in a spinal cord injured patient is significant for maintaining long term health purposes. Indeed, spinal cord injured patients lose the ability to move and thus may cause health problems such as lung and/or cardiac problems. Lack of motility also has a direct impact on the function of the intestines and thus also affects the appetite of the patient. Restoring at least partially motility in a spinal cord injured patient will help improving the overall body functions and health of the patient. It will prevent development of other disorders due to the lack of motility associated with the state of paralysis in chronic spinal cord injured patients such as lung and cardiac insufficiency, muscle atrophy, osteoporosis, lost in appetite and immune system deficiency.

Despite attempts to develop approaches and techniques to overcome problems related to spinal cord injuries and disabilities, there remains important needs in tools and therapies to at least partially restore some locomotor functions in the lower part of the body after severe spinal cord injury.

SUMMARY OF THE INVENTION

Therefore, an object of the present invention is to provide tools for inducing and restoring locomotor functions in an animal.

More specifically, that aspect is achieved by provide a composition for inducing or restoring locomotor functions in an animal, said composition comprising:
  a) more than one dopamine receptor agonist, and/or more than one noradrenaline/dopamine precursor and/or more than one serotonin receptor agonist;
  b) at least two compounds or precursors thereof selected from the group consisting of a dopamine receptor agonist, a noradrenaline/dopamine precursor, and a serotonin receptor agonist;
  c) an agent stimulating the in vivo synthesis of at least two compounds or precursor thereof selected from the group consisting of a dopamine receptor agonist, a noradrenaline/dopamine precursor, and a serotonin receptor agonist; and/or
  d) a mixture of anyone of a), b) and c).

Another object of the invention relates to a method for inducing or restoring locomotor functions in an animal, the method comprising the step of administering a therapeutically effective amount of a composition as defined above.

Yet, another object of the invention is to provide a kit for inducing or restoring locomotor functions in an animal, comprising at least two of the following compounds or precursors thereof:
  a dopamine receptor agonist;
  a serotonin receptor agonist;
  a noradrenaline/dopamine precursor;
  wherein said dopamine receptor agonist, said serotonin receptor agonist and said noradrenaline/dopamine precursor are present in an amount therapeutically sufficient to induce or restore said locomotor functions.

Figure 10:
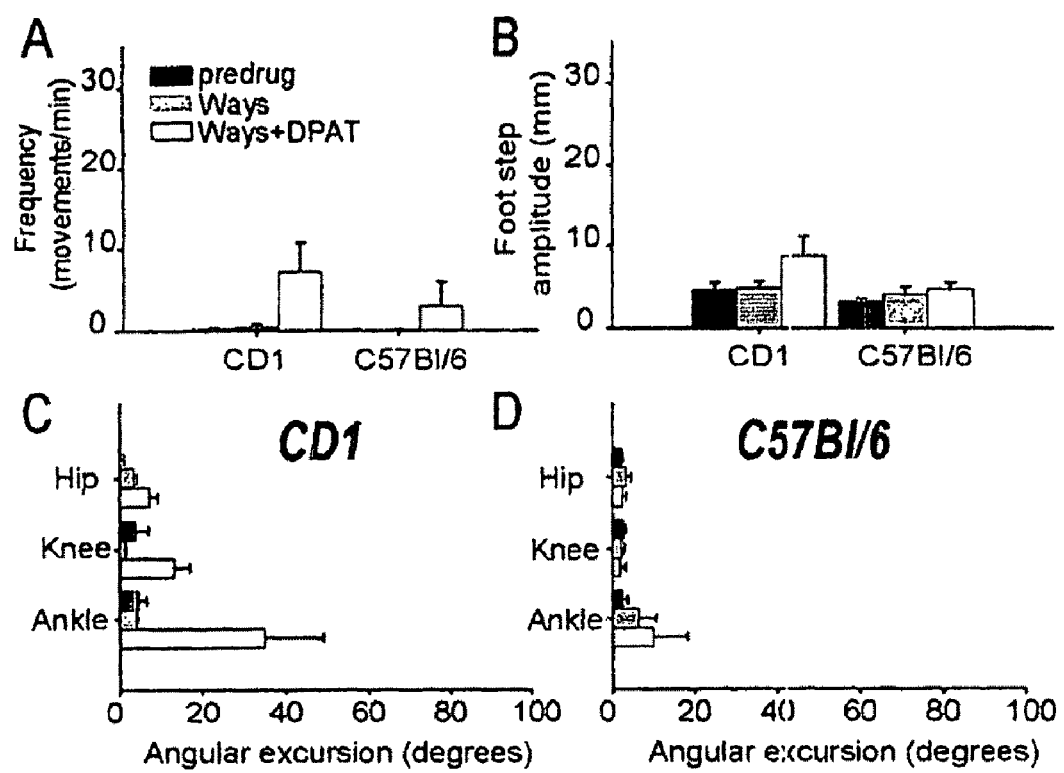

FIG. 10. Effect induced by pre-treating mice with 5-HT1A receptor antagonists (way 100,135+way 100,635) prior to 8-OH-DPAT administration. A. Largely reduced numbers of locomotor-like movements per min. B. Foot displacement amplitudes were proportionally reduced. C-D. This mostly affected the joint angular changes at the ankle level in both strains of mice.

Figure 11:
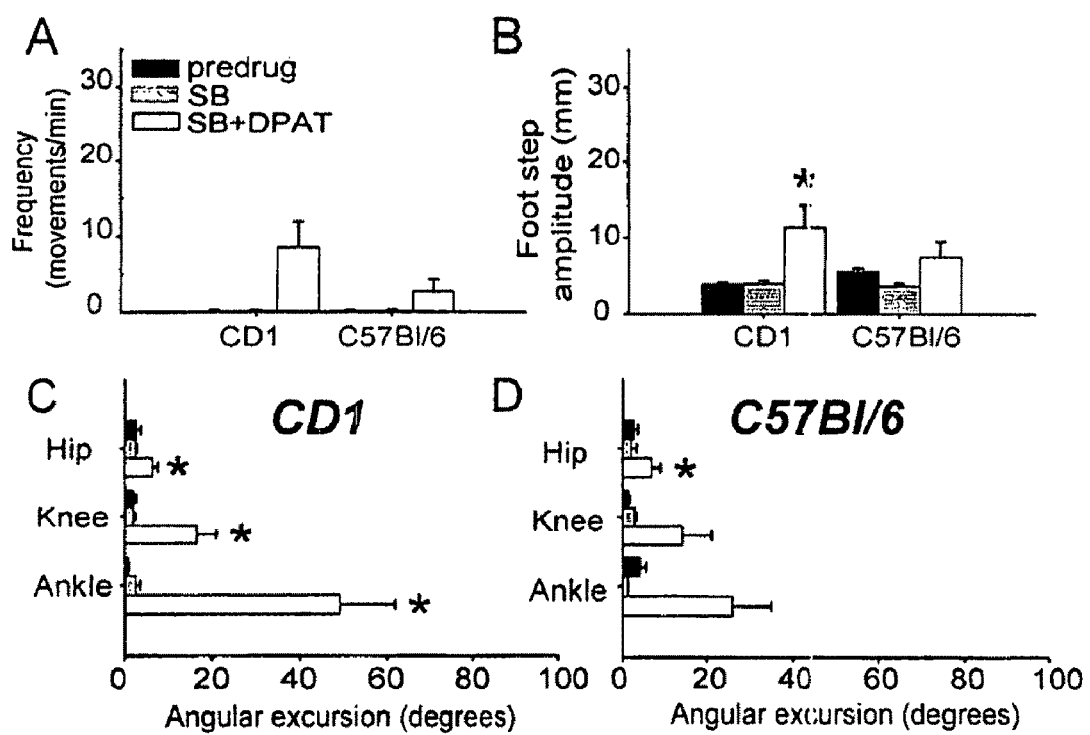

FIG. 11. Effect induced by pretreating mice with a 5-HT7 antagonist (SB269970) prior to 8-OH-DPAT administration. Movement frequencies (A), amplitudes (B) and angular excursions mostly at the ankle level were importantly reduced (C-D) in both strains.

Figure 12:
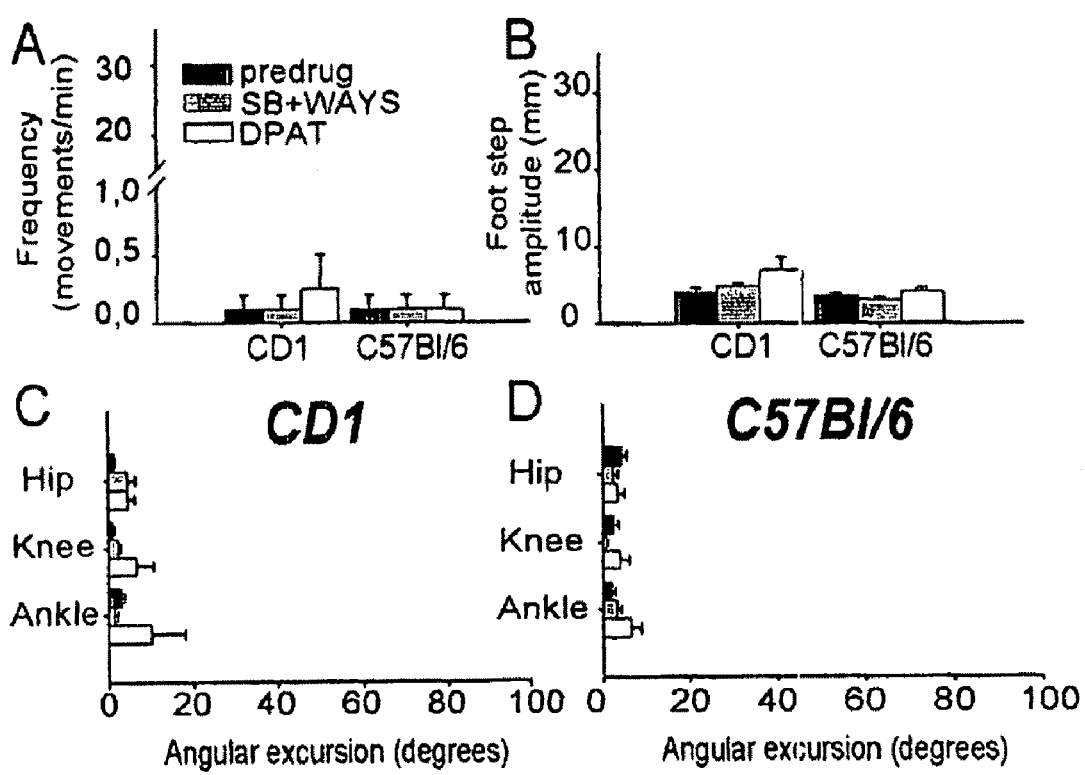

FIG. 12. Effect induced by pretreating mice with both Way100635 and SB269970 prior to 8-OH-DPAT administration. A nearly complete block of 8-OH-DPAT-induced effects on movement frequency (A), amplitude (B) and angular excursions (C-D) in both strains of mice.

Figure 13:
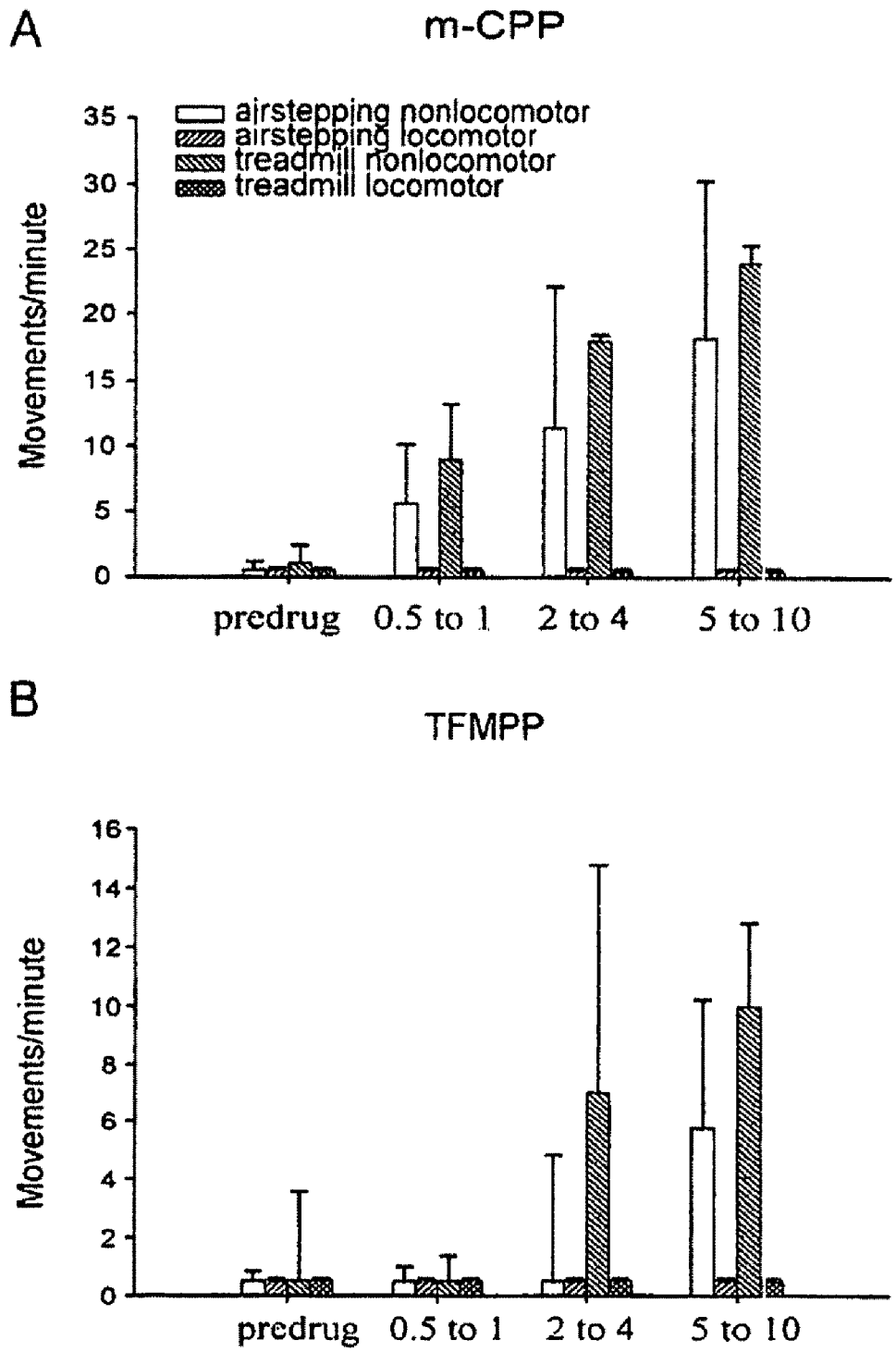

FIG. 13. Effect induced by TFMPP or m-CPP on hindlimb movement generation in paraplegic mice tested in air-stepping and treadmill conditions. A. No locomotor-like movements were induced even at high doses of m-CPP although dose-dependent non-locomotor movements were found. B. Similar lack of locomotor-like movements following TFMPP administration although non-locomotor movements were found.

Figure 14:
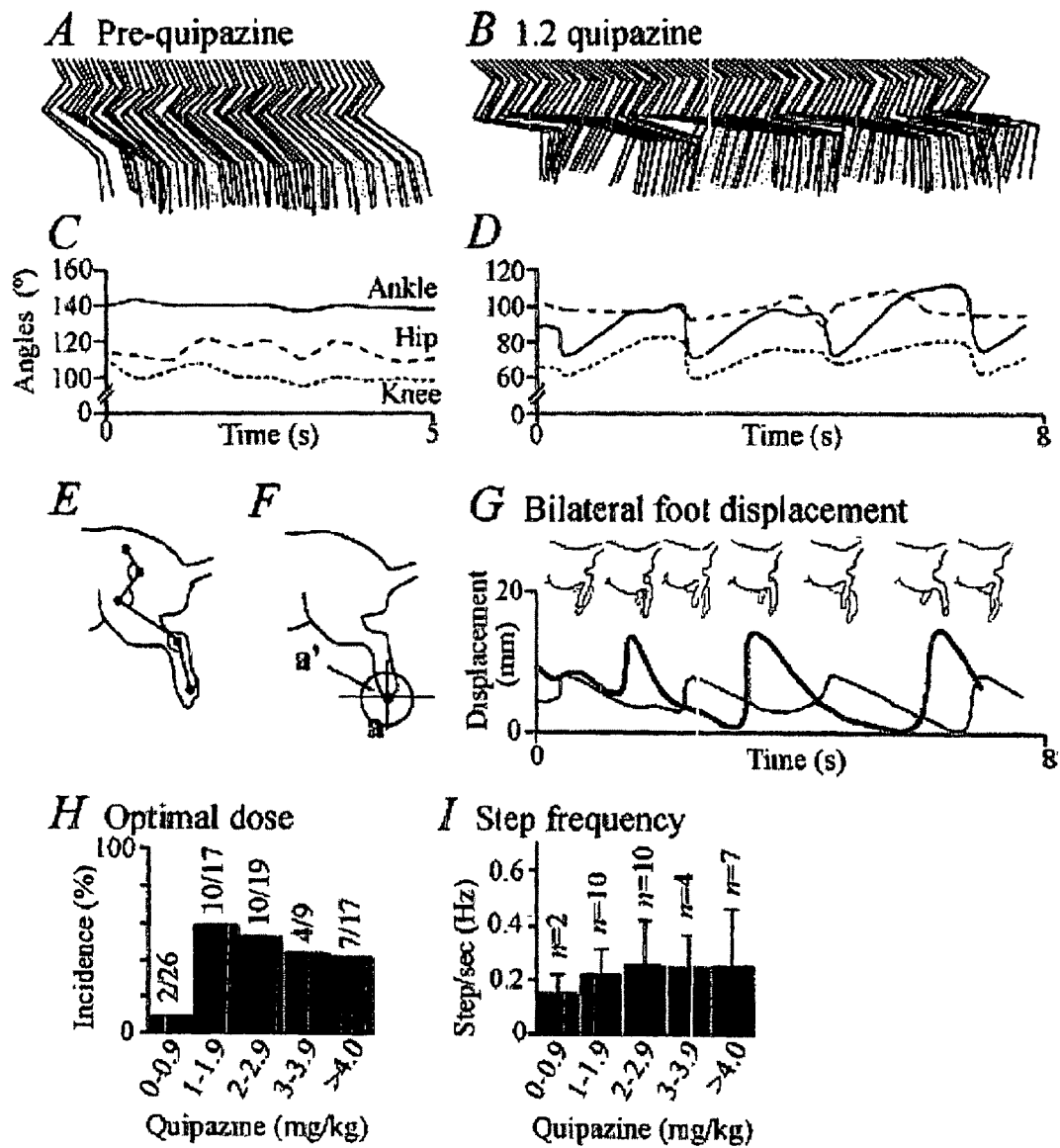

FIG. 14. Effect on hindlimb movement generation induced by quipazine in paraplegic mice. A. No hindlimb movements were found prior to quipazine administration. B. Some rhythmic flexion-extensions were found in air-stepping 20 min following an injection of 1.2 mg/kg quipazine. C-D. Corresponding changes in ankle, knee and hip angular excursions. G. Bilateral foot movement analysis revealing that both feet were moving alternatively (out-of-phase relationship). H. Doses below 0.8 mg/kg were ineffective. I. Movement frequency was not dose-dependent.

Figure 15:
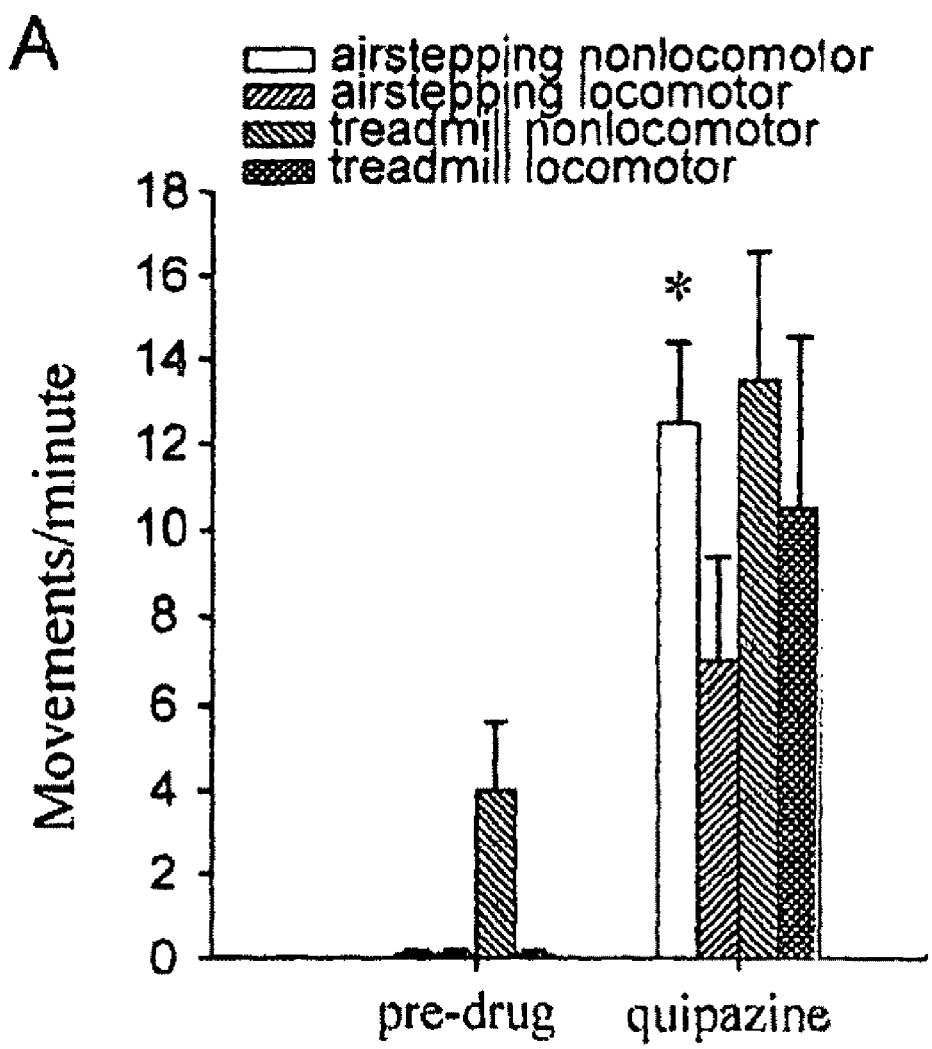

FIG. 15. Effect on hindlimb movement generation on a treadmill vs. in air-stepping induced by quipazine in paraplegic mice. A mixture of non-locomotor and of locomotor-like movements were found in mice examined both in air-stepping or on a motor-driven treadmill (8-10 cm/sec). No weight-supported stepping and plantar foot placement were found.

Figure 16:
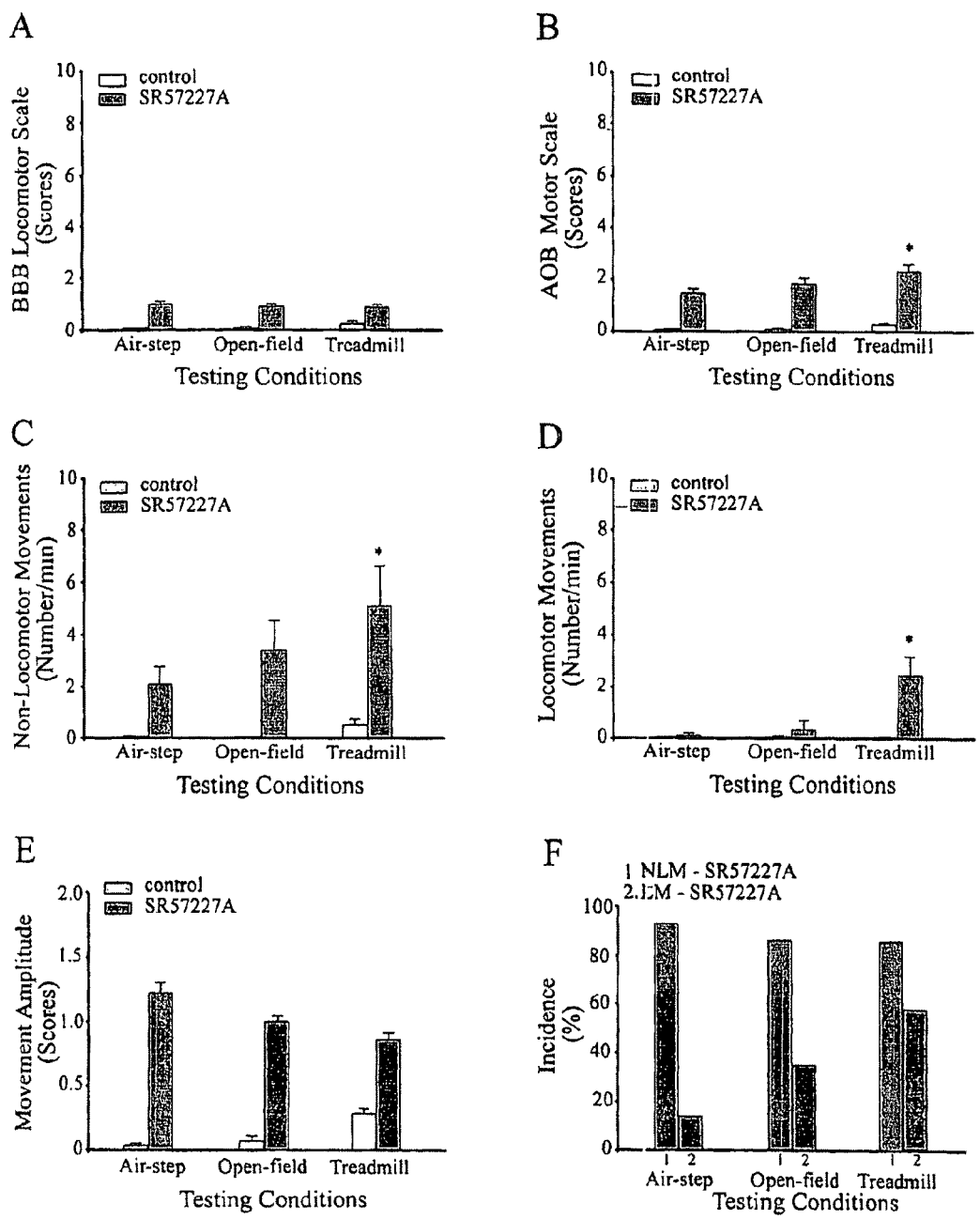

FIG. 16. Effect induced by SR-57227A (5-HT3 agonist) on hindlimb movement generation in paraplegic mice. A. Non-significant scores were found with the Basso, Beattie and Bresnahan (1996) locomotor scale. B. Some hindlimb movements corresponding to higher scores were found with the Antri, Barthe and Orsal (2002) adapted motor scale. However, these movements corresponded only non-locomotor movements in air-stepping, open-field or treadmill. Only few (approx. 2.5 per min) locomotor-like movements were found on a treadmill in some animals.

FIG. 17. Effect induced by buspirone hydrochloride (5-HT1A agonist) on hindlimb movement generation in paraplegic mice. Significant movements acutely induced by buspirone in the previously immobile hind limbs of complete paraplegic mice (8 days and 15 days post-spinalization). LM were induced with doses $\geq 6$ mg/kg.

Figure 18:
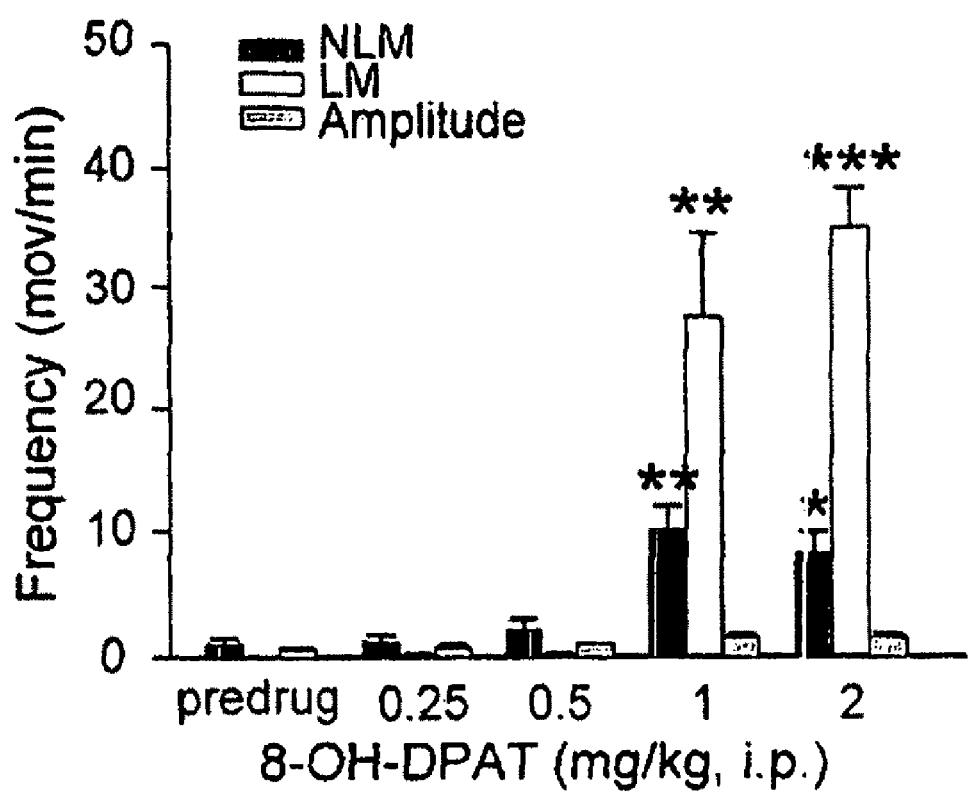

FIG. 18. Dose-dependent effect induced by 8-OH-DPAT (5-HT1A/7 agonist) on hindlimb movement generation in paraplegic mice. At lower doses ($\leq 0.5$ mg/kg), no movements were found in spinal mice tested on a treadmill. At higher doses (1-2 mg/kg), significant high numbers of LM and NLM per min were found. Rather than dose-dependent increase effects, the graph reveals an all-or-none-like effects starting with doses $\geq 1$ mg/kg. n=28.

Figure 19:
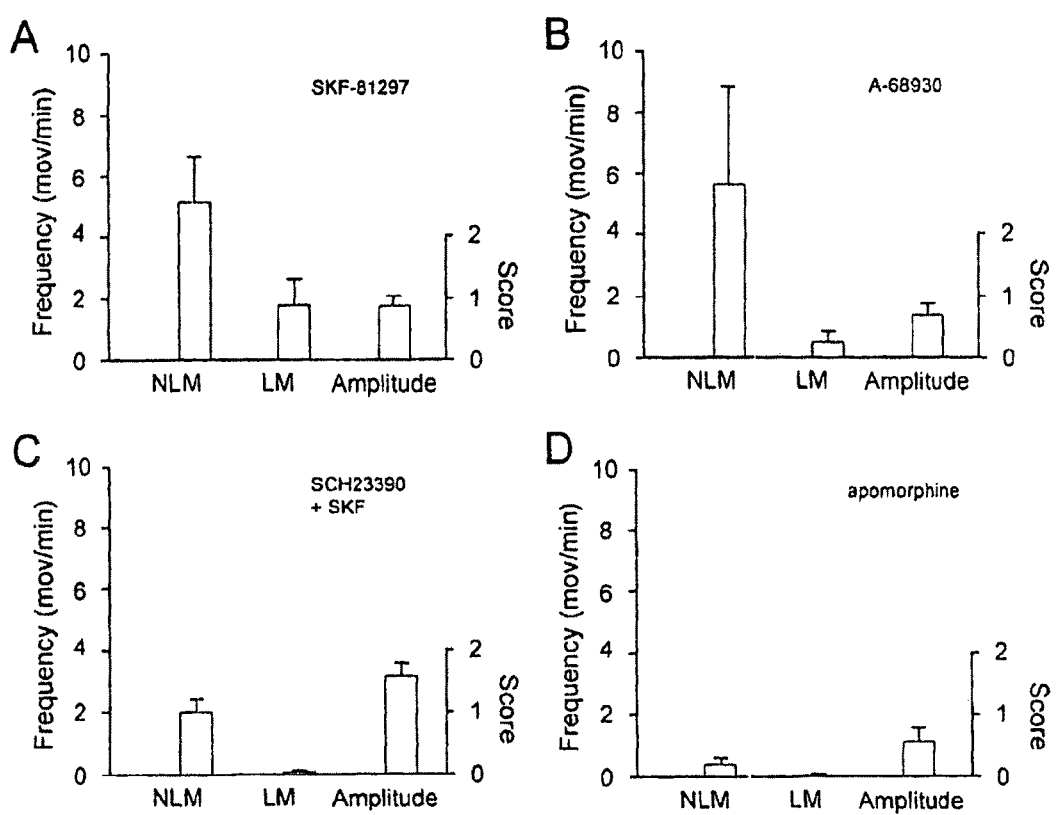

FIG. 19. Effects of partial D1 and/or D5 agonists on LM and NLM generation in paraplegic mice. Significant (P<0.05) values in all 4 cases for LM and NLM compared with pre-drug condition (i.e. immobile & pendent hindlimbs).

Figure 20:
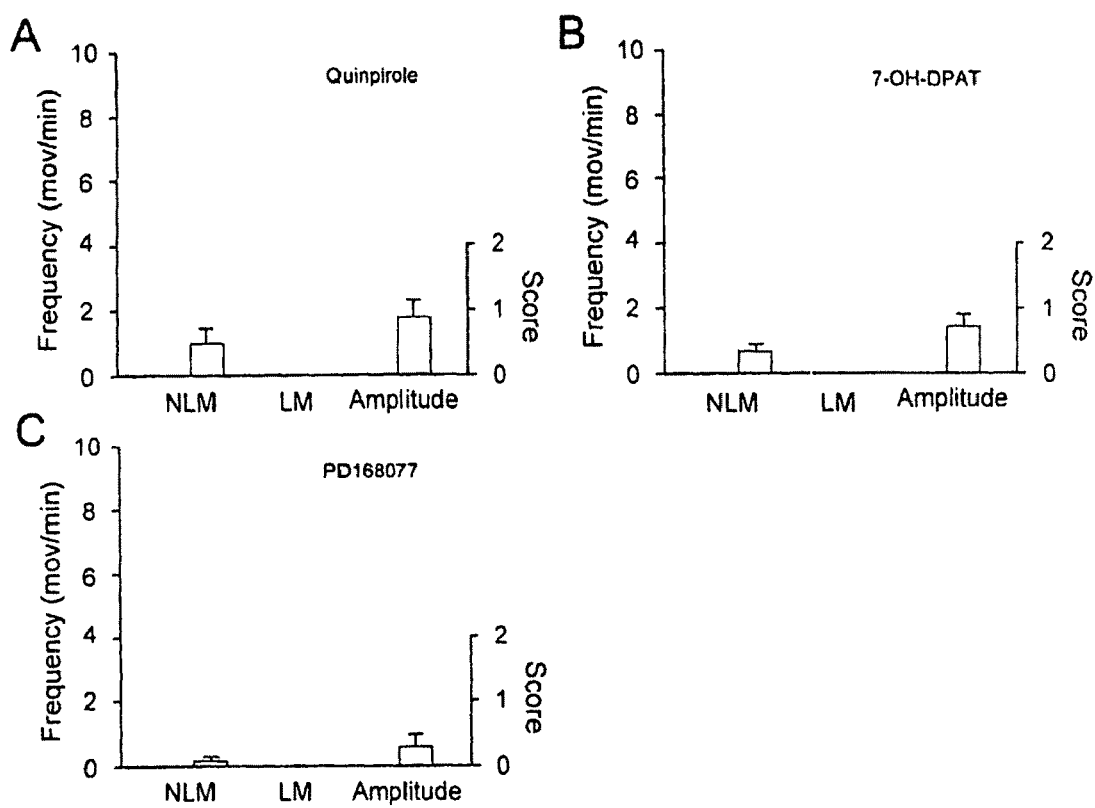

FIG. 20. Effects of partial D2, D3 and D4 agonists on LM and NLM generation in paraplegic mice. Significant (P<0.05) value in all 3 cases for NLM compared with pre-drug condition (i.e. immobile & pendent hindlimbs). Note that no LM were found.

Figure 21:
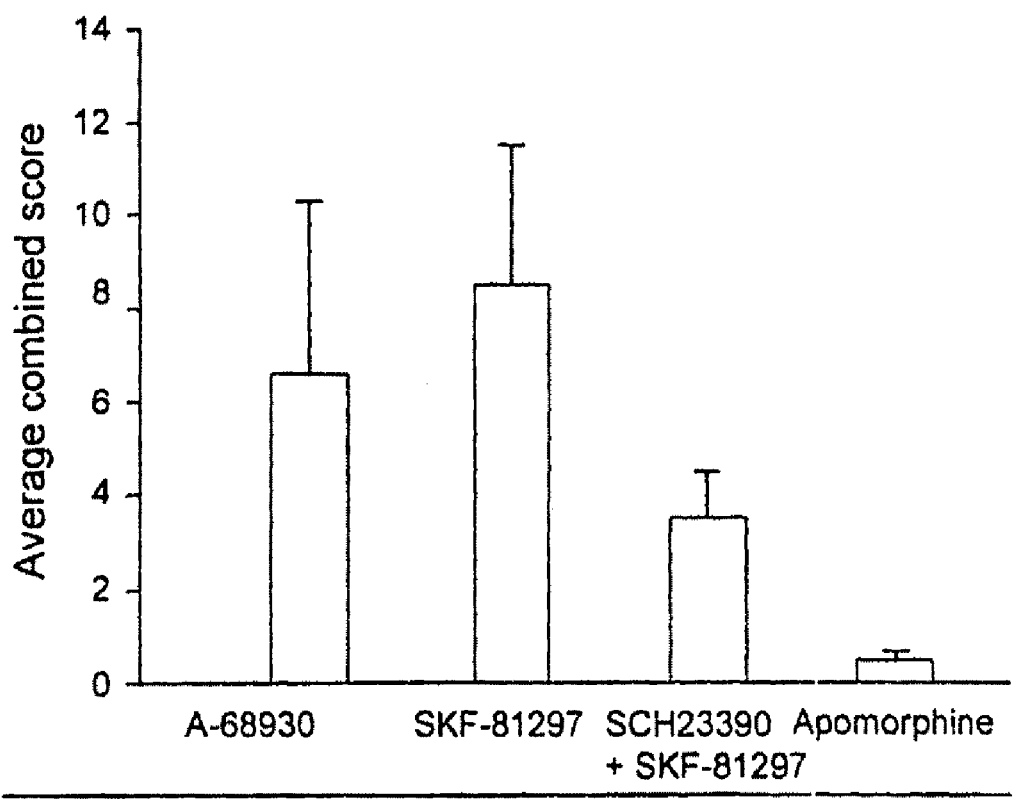

FIG. 21. Effects of partial D1 and/or D5 agonists on hindlimb movement generation in paraplegic mice. Significant (P<0.05) average combined score values in all 4 cases compared with pre-drug condition (not illustrated, see details FIGS. 19 and 20).

Figure 22A:
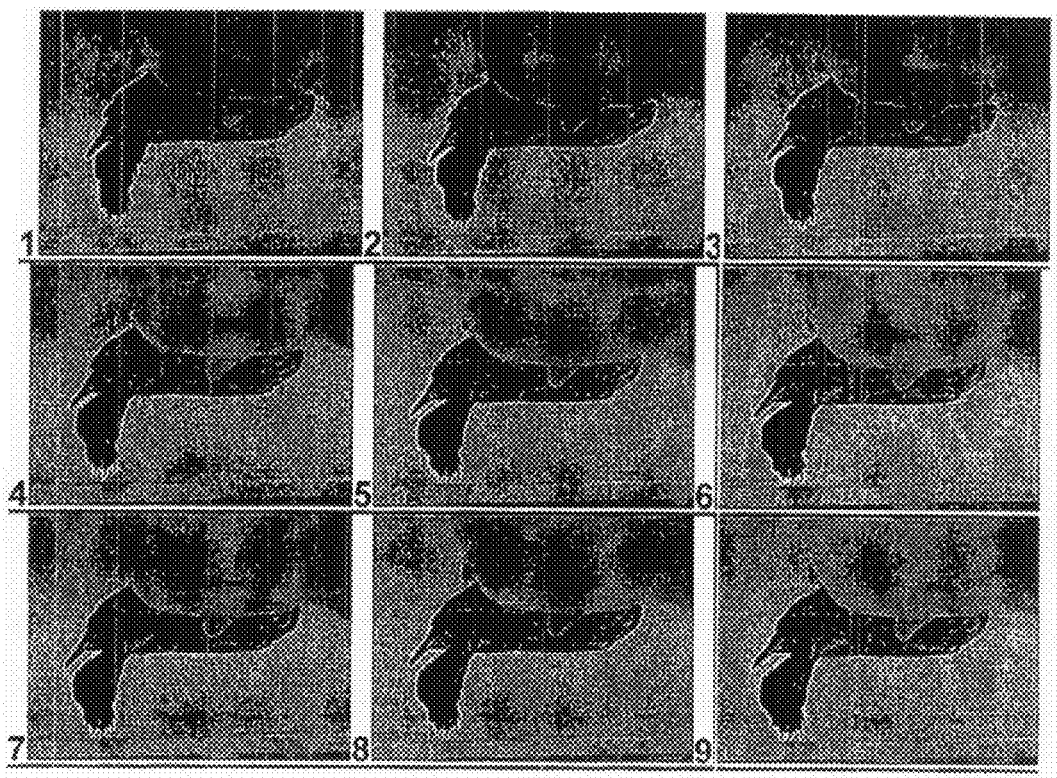
Figure 22B:
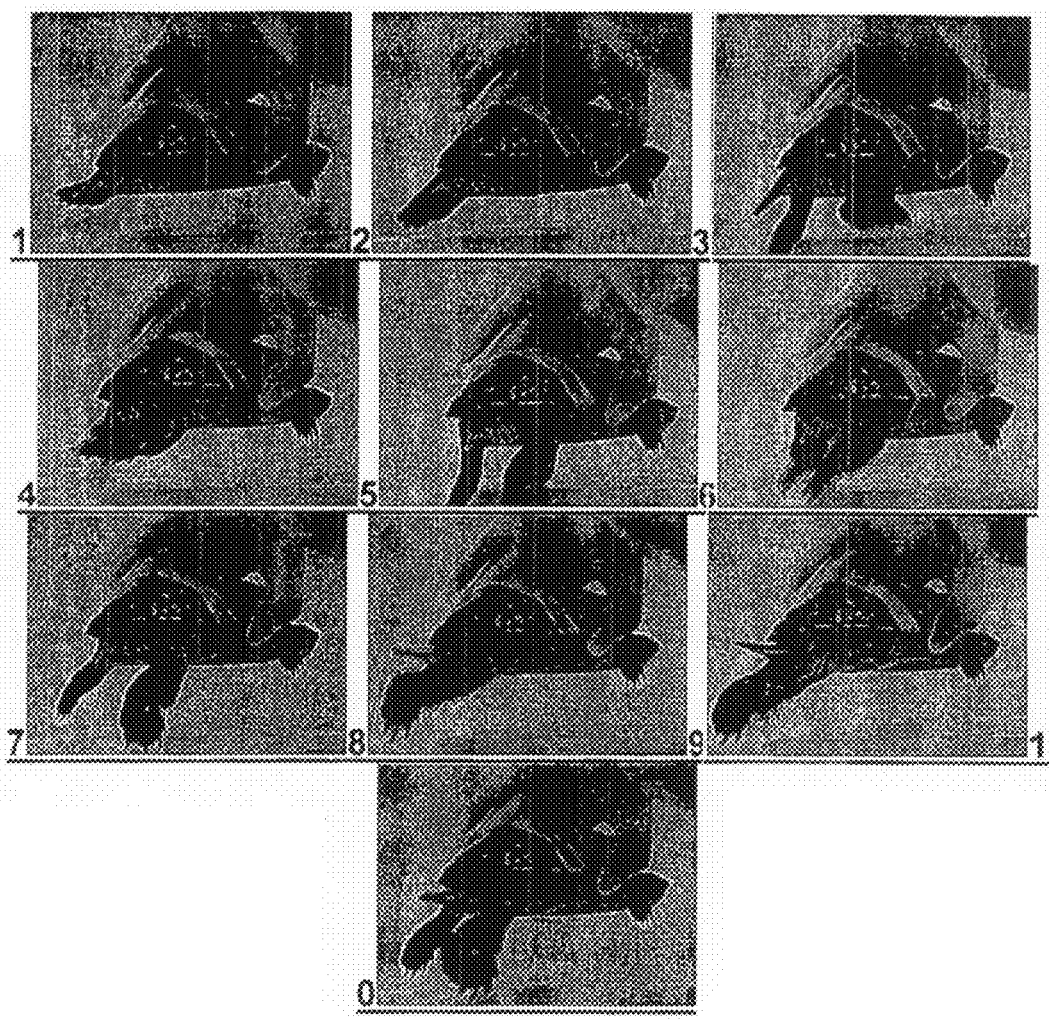

FIG. 22. Effects of 8-OH-DPAT, apomorphine, L-DOPA (benserazide) in 1-day spinal turtles. A. Lack of movements prior to drug injection. B. Rhythmic locomotor (swimming-like) movements induced 20 min post-drug injection.

DETAILED DESCRIPTION OF THE INVENTION

The inventor has discovered that the administration of a composition, which will be detailed hereinafter, stimulates motor functions or the lower body part muscles. More particularly, it has been demonstrated that the administration of an effective amount of the composition according to the present invention to a spinal cord injury victim, such as a paraplegic animal, promotes locomotor recovery or inhibits locomotor damage or limits locomotor impairment following chronic spinal cord injury.

The composition of the invention may be particularly advantageous for instance in the treatment and/or training of paraplegic or tetraplegic individuals on a treadmill in order to prevent and treat osteoporosis (osteopenia), muscle weakness and atrophy, spasticity, cardiovascular problems and immune system deficiency that are generally associated with the state of paralysis in chronic spinal cord injured patients.

The composition and method of the present invention are also useful for treating impaired locomotor function-derived disorders, such as but not limited to, multiple sclerosis (MS), amyotrophic lateral sclerosis (ALS), cerebro-vascular diseases or trauma and other neurological disorders.

Definitions

As used herein, the expression "inducing locomotors functions" means an apparition shortly for instance (10-20 min) after drug administration of rhythmic movements characterized by successive flexions and extensions with bilateral alternation in the previously immobilized hindlimbs of paralyzed animals. It is characterized also by regular stepping activity with at least occasional to frequent weight-bearing capabilities and occasional to frequent plantar foot placements.

The expression "restoring locomotor functions" as used herein means a return of locomotor functions as defined above.

It will also be understood that the scope given to the expression "locomotor functions" is a synonym of the expression "rather well-coordinated and self-sustained walking movements".

The expressions defined above are in contrast with the more limited definition of "locomotor-like movements" or LM (see hereinbelow). Indeed, the expression "locomotor-like movements" or LM refers to hindlimb movements sharing only some characteristics of complete locomotor functions. The term "locomotor-like movements" is defined as hindlimb movements constituted of even small flexions and extensions of the hindlimbs (e.g. involving one or several joints) occurring in both hindlimbs with alternation. LM do not include self-sustained weight bearing stepping or adequate plantar foot placement (but only dorsal foot placement). Therefore, LM in quadrupedal paraplegic animals, for instance, resemble to sweeping (even of weak amplitude) rather than to real walking.

In any case, none of the movements induced by these drugs in complete paraplegic or tetraplegic animals are expected to include full self-maintained lateral stability, as equilibrium is partially under the control of the cerebellum (postero-inferior part of the brain) which can not any more participate to the maintenance of lateral stability in complete spinal animals due to the lesion between the lumbar locomotor networks and all brain structures.

As used herein, the term "animal" refers to any animal that has suffered an injury to its spinal cord and has lost some voluntary motor function as a consequence of the injury. Such an animal may be classified as a mammal, such as humans, domestic and farm animals, and zoo, sports, or pet animals. Preferably, the contemplated animal is human.

As used herein the expression "partly selective" means: receptor agonists that generally binds to several subtypes of receptors rather than to mainly only one receptor subtype.

By "derivative", it is meant any compound that possesses a functional biological activity that is substantially similar to the biological activity of the preferred dopamine receptor agonist, noradrenaline/dopamine precursor or serotonin receptor agonist.

Composition of the Invention

In accordance with the present invention, there is provided a composition for inducing or restoring locomotor functions in an animal.

The composition of the invention comprises:
a) more than one dopamine receptor agonist, and/or more than one noradrenaline/dopamine precursor and/or more than one serotonin receptor agonist;
b) at least two compounds or precursors thereof selected from the group consisting of a dopamine receptor agonist, a noradrenaline/dopamine precursor, and a serotonin receptor agonist;
c) an agent stimulating the in vivo synthesis of at least two compounds or precursor thereof selected from the group consisting of a dopamine receptor agonist, a noradrenaline/dopamine precursor, and a serotonin receptor agonist; and/or
d) a mixture of anyone of a), b) and c).

According to a first preferred embodiment of the invention, the composition comprises at least two compounds or precursors thereof selected from the group consisting of a dopamine receptor agonist, a noradrenaline/dopamine precursor, and a serotonin receptor agonist. Thus, compositions comprising more than one dopamine receptor agonist, and/or more than one noradrenaline/dopamine precursor and/or more than one serotonin receptor agonist are within the scope of the invention.

According to a second preferred embodiment, the composition comprises a dopamine receptor agonist, a noradrenaline/dopamine precursor and a serotonin receptor agonist.

In accordance with the present invention, the dopamine receptor agonist is preferably selected from the group consisting of apomorphine, ropinirole, pramipexole, pergoline, cabergoline, SKF-81297, and analogs, derivatives or combinations thereof. More preferably, the dopamine receptor agonist is apomorphine. Apomorphine, having the general formula ((R)-5,6,6a,7-tetrahydro-6-methyl-4H-dibenzo-[de,g] quinoline-10,11-diol), can be used in a free base form or as an acid addition salt. For the purposes of the present invention, apomorphine hydrochloride is preferred, however other pharmacologically acceptable salts thereof can be utilized as well.

Apomorphine can be generally used in the form of pharmaceutically acceptable salts derived from inorganic or organic acids. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salts. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In accordance with the present invention, the noradrenaline/dopamine precursor is preferably selected from the group consisting of L-DOPA, phenylalanine, tyrosine, L-threo-3,4-dihydroxyphenylserine, analogs, and derivatives or combinations thereof. More preferably, the nordrenaline/dopamine precursor is L-DOPA. L-DOPA is also known as levodopa, chemically known also as L-(−)-2-amino-3-(3,4-dihydroxyphenyl)propionic acid or as 3,4-dihydroxyphenyl-L-alanine or as 3-hydroxy-L-thyrosine, which is an aminoacid of natural origin known since long time for its pharmacological activity in the treatment of the Parkinson's disease. In a preferred embodiment, L-DOPA is combined with a decarboxylase inhibitor such as benserazide (for instance with a ratio of 4:1) to increase central nervous system availability of the drug upon systemic administration.

In accordance with the present invention, the serotonin receptor agonist is preferably selected from the group consisting of buspirone, 8-OH-DPAT, 5-CT, metergoline, pimozide, AS19, and another agonist partially selective at the 5-HT1, 5-HT2, 5-HT3, 5-HT4 and 5-HT7 receptor subtypes. More preferably, the serotonin receptor agonist is buspirone or 8-OH-DPAT (8-hydroxy-2(di-n-propylamino)-tetralin) or derivatives thereof. Most preferably, the serotonergic agonist is a 5-HT1A receptor agonist, namely buspirone or derivatives thereof.

It will be understood to anyone skilled in the art that the composition of the present invention may be a mixture of at least two of the three compounds described herein, dissolved or administered with a pharmaceutical acceptable carrier or solvent.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate.

Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of recombinant expression vectors may be lyophilized using means well known in the art, for subsequent reconstitution and use according to the invention.

Method of Use

The present invention provides a method for inducing or restoring locomotor functions in an animal, the method comprising the step of administering a therapeutically effective amount of a composition as defined above.

The composition of the invention may be given to an animal through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection, by infusion or per os. The composition of the invention may also be administered into the airways of a subject by way of a pressurized aerosol dispenser, a nasal sprayer, a nebulizer, a metered dose inhaler, a dry powder inhaler, or a capsule. Suitable dosages will vary, depending upon factors such as the amount of each of the components in the composition, the desired effect (short or long term), the route of administration, the age, the metabolism and the weight of the animal to be treated.

The amount of compounds present in the composition of the present invention is preferably a therapeutically effective amount. A therapeutically effective amount of the compounds is that amount necessary to excite cells in the lumbar spinal cord region in order to allow the composition of the invention to perform its locomotor function inducing or restoring role without causing, overly negative effects in the animal to which the composition is administered. The exact amount of compounds to be used and the composition to be administered will vary according to factors such as the type of condition being induced or restored, the mode of administration, as well as the other ingredients in the composition.

An anticipated preferred dose of the composition of the present invention may be from about 0.1 to about 1 mg/kg of dopaminergic agonist, from about 5 to about 50 mg/kg of noradrenaline/dopamine precursor, and of about 0.1 to about 1 mg/kg of serotonergic agonist of body weight, with dosage being dependent upon a number of factors including the species of animal, the animal's susceptibility to stimuli, and the nature of the stimulus.

Kits

The present invention further provides kits for use within the above described method. Such kits typically comprise two or more components necessary for inducing or restoring locomotor functions. Components may be compounds, reagents, containers and/or equipment.

In this connection, the present invention provides a kit for inducing or restoring locomotor functions in an animal, comprising at least two of the following compounds or precursors thereof:
a dopamine receptor agonist;
a serotonin receptor agonist; and/or
a noradrenaline/dopamine precursor;
wherein said dopaminergic agonist, said serotonergic agonist and said noradrenaline/dopamine precursor are present in an amount therapeutically sufficient to induce or restore said locomotor functions.

EXAMPLES

The present invention will be more readily understood by referring to the following examples. These examples are illustrative of the wide range of applicability of the present invention and is not intended to limit its scope. Modifications and variations can be made therein without departing from the spirit and scope of the invention. Although any methods and materials similar or equivalent to those described herein can be used in the practice for testing of the present invention, the preferred methods and materials are described.

Example 1

Acute Effects Induced by a Combined Treatment Including a Dopamine/noradrenaline precursor (+a Peripheral Decarboxylase Inhibitor), a Serotonin Receptor Agonist, and a Dopamine Receptor Agonist on Hindlimb Movement Generation in Spinal Cord Injured Mice.

Materials and Methods

Animals and Treatment Thirty-two (n=32) male or female adult CD1 mice weighing 30-40 grams were tested prior to the study (Charles River Laboratory, St-Constant, Canada). The experiment was conducted in a Canadian Council on Animal Care approved facility in accordance with the CCAC Guide for Care and Use of Experimental Animals. Animals were spinalized 7-9 days prior to testing. A complete transection of the spinal cord was performed intervertebrally between the $9^{th}$ and $10^{th}$ vertebrae in isoflurane (2.5%) anesthetized animals. Complete spinalization was confirmed by 1) full paralysis of the hindlimbs, 2) post-mortem examination of the spinal cord microscopically and, in some cases, 3) staining transverse or sagittal spinal cord sections with luxol fast blue/cresyl violet for myelinated axons and nissl substance respectively. All mice received pre-operative care and post-operative care including lactate-Ringer's solution (2 ml/day, s.c.), analgesic (buprenorphine 0.2 mg/kg/day, s.c.) and antibiotic (baytril 5 mg/kg/day, s.c.). Bladders were emptied manually and animals were left in their cage without other interventions with food and water ad libitum until testing. Mice received a single injection i.p. of L-DOPA/benserazide+5-HT agonist (8-OH-DPAT or buspirone)+a dopamine receptor agonist (apomorphine or SKF 81297).

Hindlimb movement recording. Hindlimb movements were filmed (digital video camera 3 Com Home-connect, 30 frames/sec), 1) immediately prior to injection and, 2) at fixed delays after injection in animals placed on a treadmill running at a speed of 8-10 cm/sec (treadmill condition). A harness was put around the torso and the waist to maintain them in front of the camera on the treadmill (not weight support was provided). Animals were not stimulated otherwise. Hindlimb movements were assessed either as locomotor-like movements (LM) or non-locomotor movements (NLM) Locomotor-like movements were defined as rhythmic flexions and extensions occurring in both hindlimbs alternatively. Body weight support and plantar foot placement were facultative and therefore not required to be counted as locomotor-like (LM). In turn, non-locomotor movements (NLM) were defined as non-bilaterally alternating hindlimb movements most often including spasms, kicks, uncoordinated or unilateral movements, etc. Levels of weight supported movements and of plantar foot placements were assessed as either none, occasional, or frequent.

Statistical analyses. Paired Student's t tests or one-way ANOVA were performed.

Results

Figure 1A:
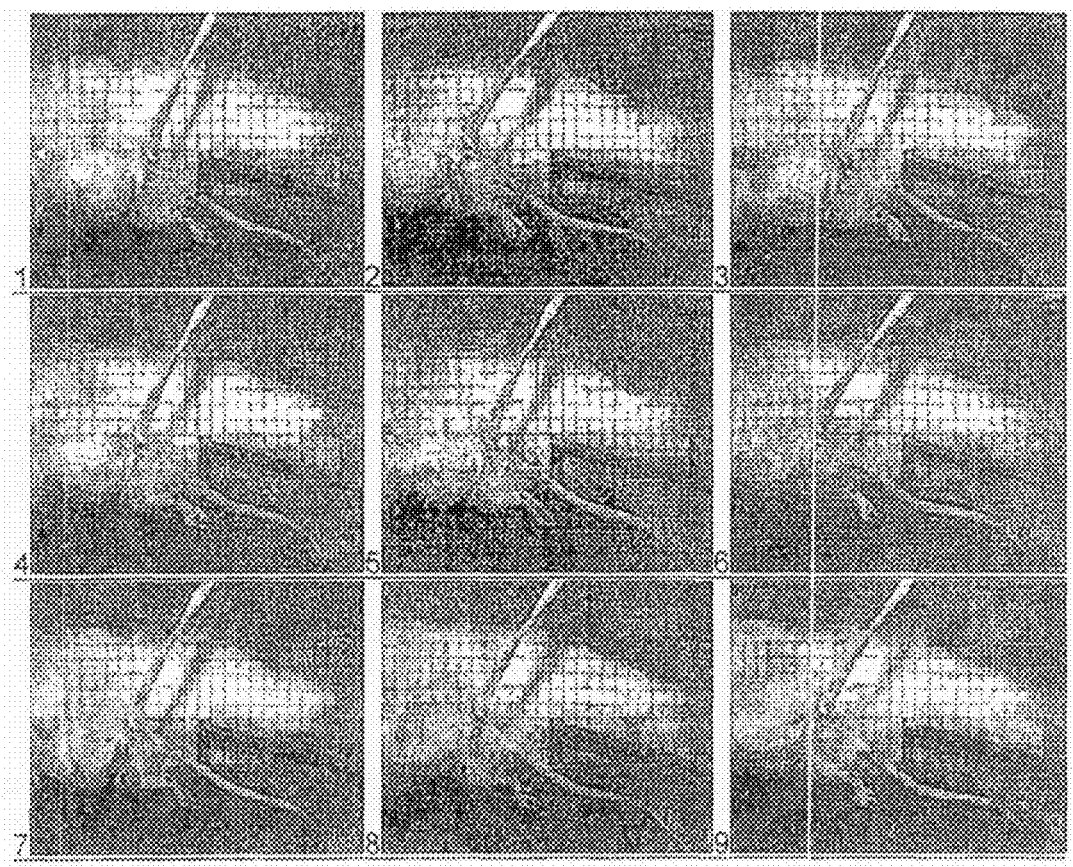
FIG. 1. Effects induced after injection of 40 mg/kg L-DOPA (+benserazide 10 mg/kg), 1 mg/kg Apomorphine, and 1 mg/kg 8-OH-DPAT on LM and NLM generation in a paraplegic mouse. A. Lack of movements before treatment administration. B. Hindlimb locomotor movements (LM) including full body weight supported steps and adequate plantar foot placement were induced 15 min following drug administration. C. 1 h 15 later, the effects gradually disappeared.
Figure 1B:
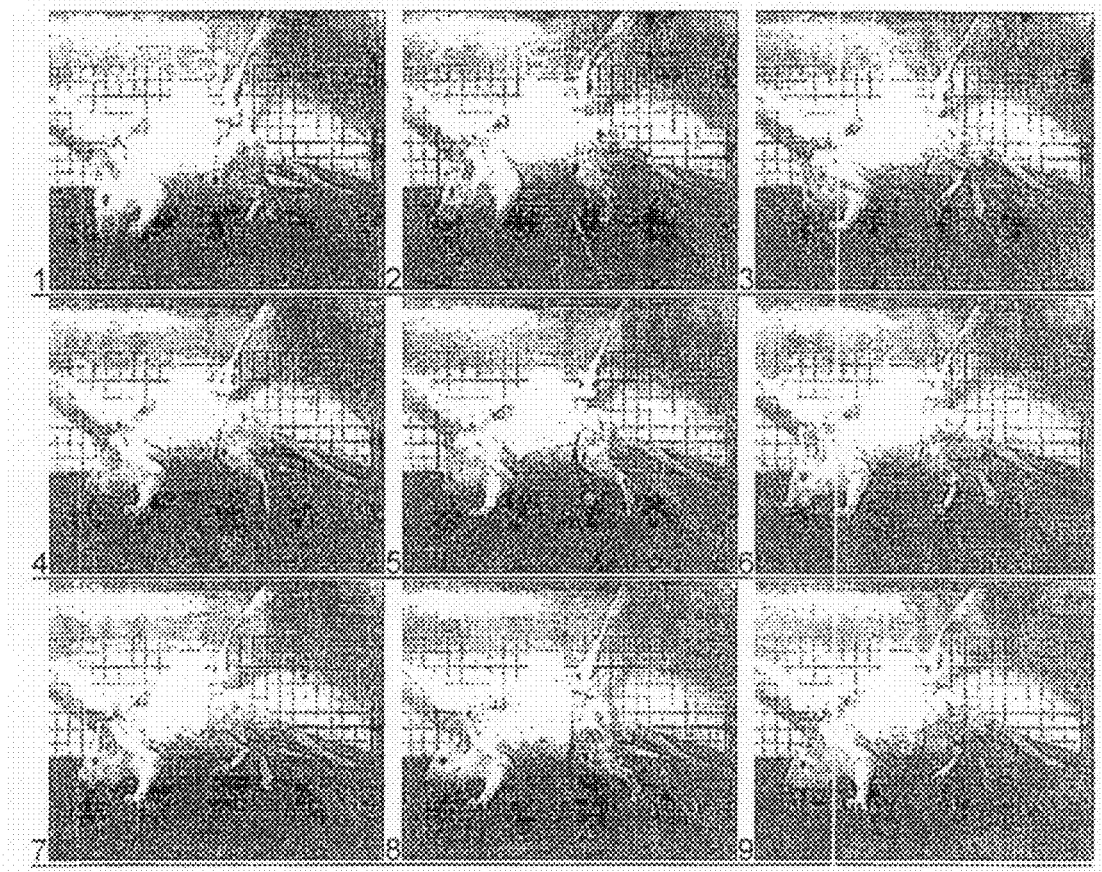
Figure 1C:
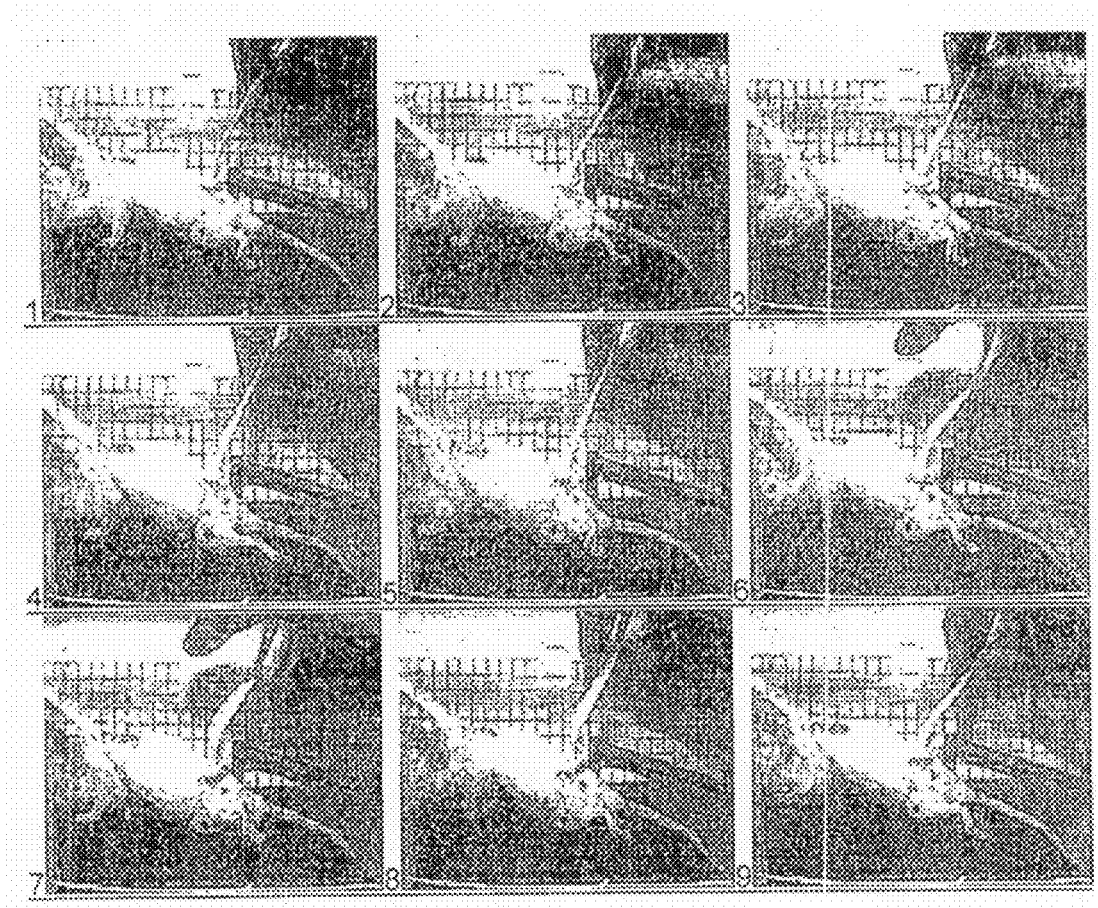

L-DOPA (/benserazide)+apormorphine+8-OH-DPAT: We found in 7/8 mice that LM and NLM were induced by a single dose of the treatment (40-60 mg/kg L-DOPA/10-15 benserazide+1-2 mg/kg apomorphine (D1/D2-like agonist)+1-2 mg/kg 8-OH-DPAT (5-HT1A/7 agonist). This is illustrated with a typical example in FIG. 1. FIG. 1A shows that no movement were found in a complete paraplegic mouse just prior to treatment administration. FIG. 1B, the treatment acutely induced shortly after administration, a combination of NLM and LM. On average (n=7/8 mice), 24.6. LM per min and 13.3 NLM per min were found to be induced. On average, LM included frequent weight supported steps accompanied with occasional plantar foot placement. Approximately 1 h 15 min later, the efficacy of the treatment disappeared as small amplitude movements with no bilateral coordination were found (FIG. 1C).

Figure 2:
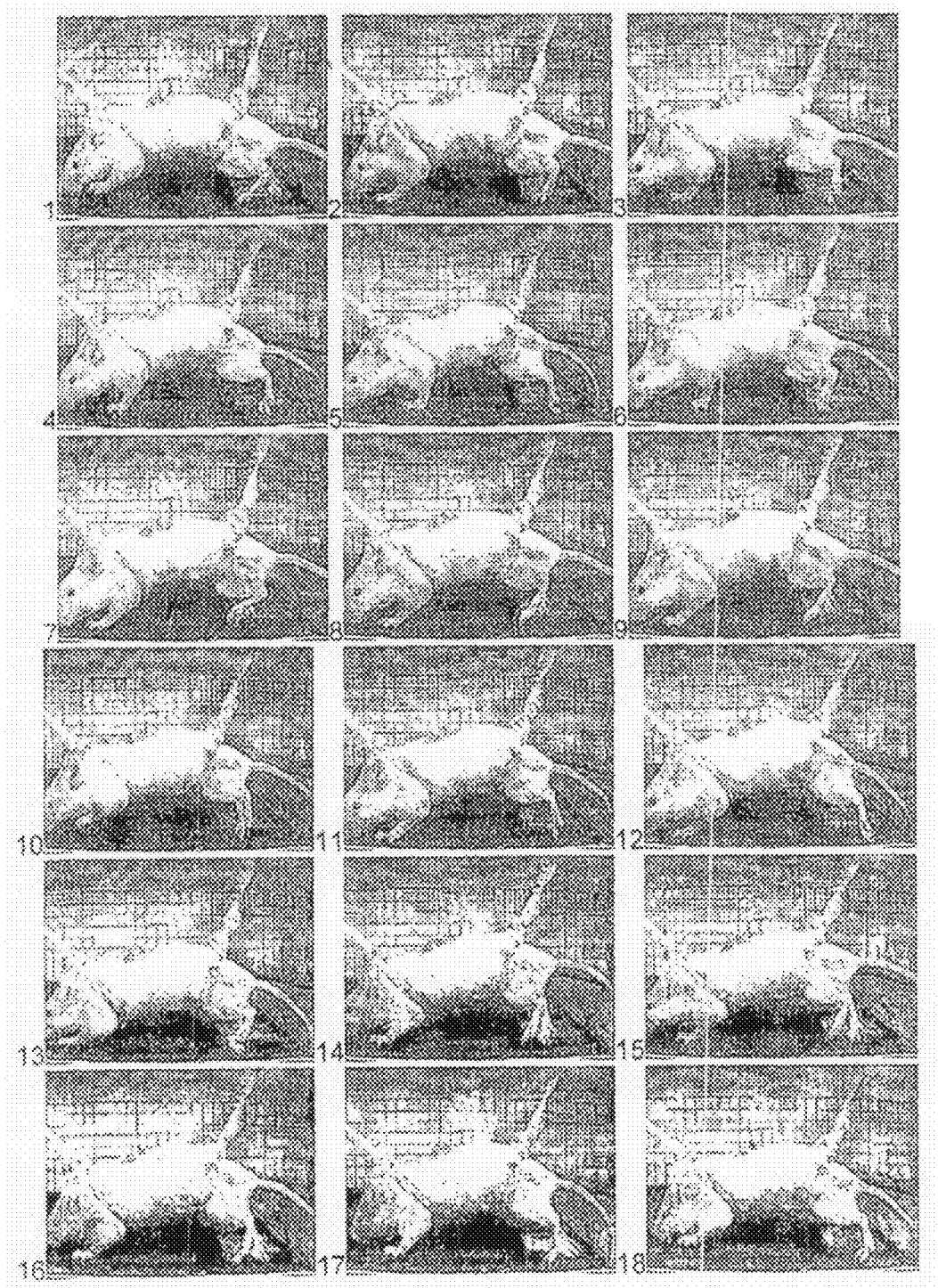
FIG. 2. Effects induced by 60 mg/kg L-DOPA (+benserazide 15 mg/kg), 3 mg/kg SKF-81297, and 3 mg/kg 8-OH-DPAT in a paraplegic mouse. We show 2 step cycles (within a 2 sec-period) representative of the effects. This mouse displayed 33 locomotor-like movements (LM) and 12 non-locomotor movements per min during approximately 1 hour. No weight support assistance or other stimulation was provided.

L-DOPA (/benserazide)+SKF 81297+8-OHDPAT: We found in all mice tested (8/8) that LM and NLM were induced by a single dose of the treatment (40-60 mg/kg L-DOPA/10-15 benserazide+1-3 mg/kg SKF 81297 (D1/D5 agonist)+1-3 mg/kg 8-OH-DPAT (5-HT1A/7 agonist). This is illustrated with a typical example in FIG. 2 where a combination of NLM and LM were found to be induced after a single treatment. On average (n=8 mice), 21.3 LM per min and 10.8 NLM per min were found to be induced. On average, LM included occasional body weight supported steps accompanied with occasional plantar foot placement. Approximately 1 h 00-1 h 15 min later, the efficacy of the treatment disappeared as small amplitude movements with no bilateral coordination were found.

Figure 3:
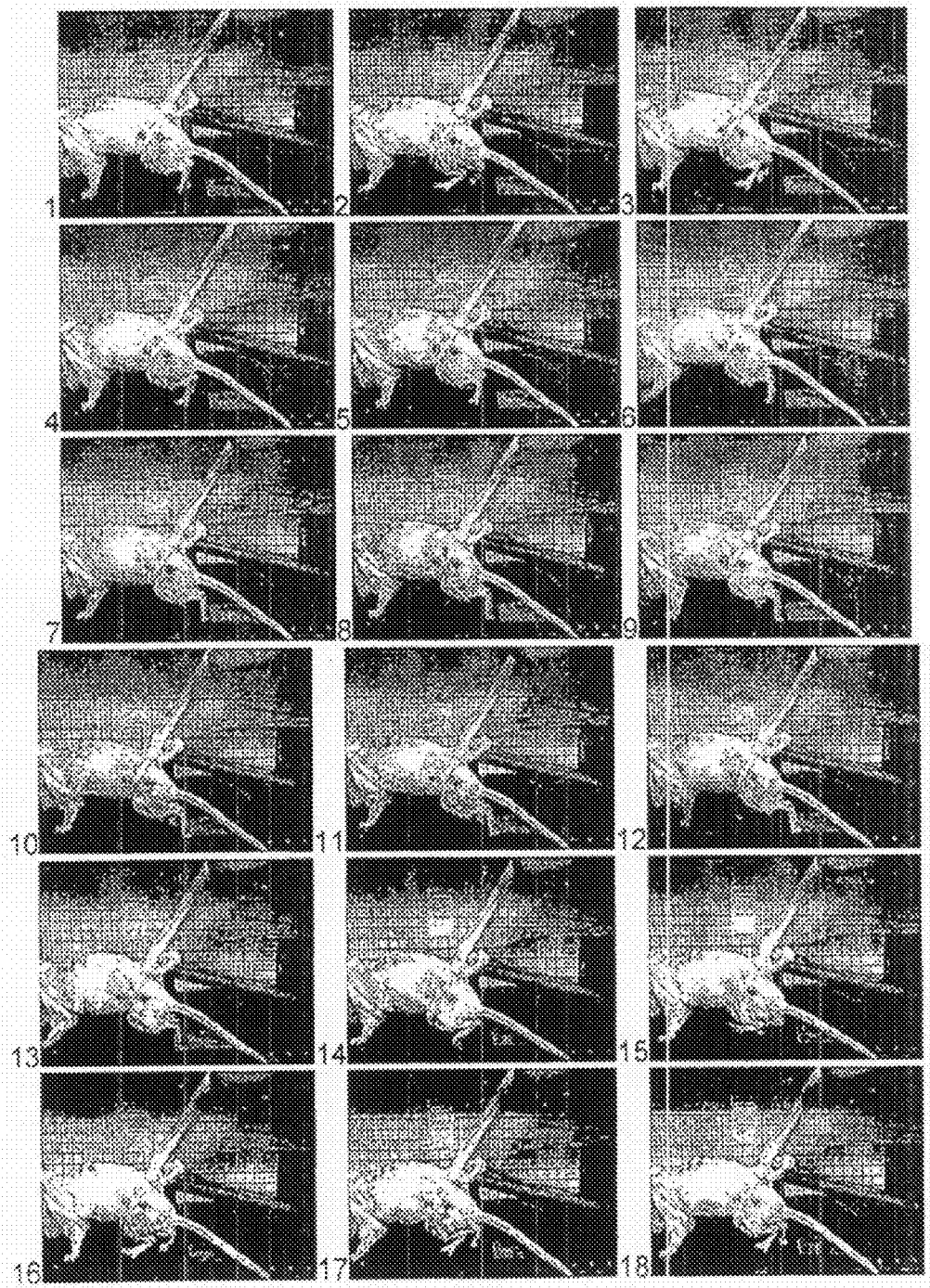
FIG. 3. Effects induced after infection of 45 mg/kg L-DOPA (+benserazide 10 mg/kg), 2 mg/kg Apomorphine, and 2 mg/kg Buspirone on LM and NLM generation in a paraplegic mouse. Two of the step cycles performed are illustrated with 18 pictures covering a 3-sec period of activity chosen randomly. Overall, this mouse displayed 10 min post-injection 29 locomotor-like movements (LM) and 6 non-locomotor movements per min. No weight support assistance or other stimulation was provided. Regular and steady weight-supported stepping with plantar foot placement was induced with this treatment. Effects disappeared completely 1 h 20 min later (not shown)

L-DOPA (/benserazide)+Apomorphine+Buspirone: We found in 14/16 paraplegic mice tested (8/9 male and 6/7 female CD1) that a single injection of 40-50 mg/kg L-DOPA (+benserazide 10 mg/kg), 1-2 mg/kg Apomorphine (D1/D2-like agonist), and 1-2 mg/kg Buspirone (5-HT1A agonist) induced locomotor-like (LM) as well as some non-locomotor movements (NLM). In approximately half of these mice (7/16), LM included steady weight supported stepping movements (with no assistance from the experimenter for weight support) accompanied with nearly normal plantar foot placement (see FIG. 3). These effects were found within 10-15 min post-administration and disappeared completely 1-1 h 30 later. On average, this combination of drugs induced 13.9 LM per min (n=14/16) and 12.5 NLM per min (16/16 mice) in the previously completely immobilized hindlimbs of these paraplegic mice.

Conclusion

The results of this example showed that administration of a precursor of dopamine/noradrenaline synthesis+a dopamine receptor agonist (preferably with binding affinity for the D1 and D5 receptor subtypes)+a serotonin receptor agonist (preferably with binding affinity for the 5-HT1A, 5-HT7) can powerfully generate within 10-15 min hindlimb stepping movements with some body weight support and plantar foot placement. Preferably the combined treatment will include L-DOPA (+benserazide)+Apomorphine (D1/D2-like agonist)+Buspirone (5-HT1A agonist). It can also be composed, for instance, of L-DOPA/benserazide+Apomorphine (D1/D2-like agonist)+8-OH-DPAT (5-HT1A/7 agonist) or of L-DOPA/benserazide+SKF-81297 (D1/D5 agonist)+8-OH-DPAT (5-HT1A/7 agonist). This combination was therefore shown to act in synergy to powerfully and properly activate the lumbar spinal cord circuitry for hindlimb locomotion in paraplegic mice since drug-induced large amplitude LM accompanied also of weight-bearing capabilities and plantar foot placement.

Example 2

Effect Induced by L-DOPA Used Individually on the Induction of Leg Locomotor Movements in Spinal Cord Injured Mice Materials and Methods Animals and Treatment. Twenty-nine (n=29) male and female adult CD1 mice weighing 30-40 grams prior to the study (Charles River Laboratory, St-Constant, Canada). The experiment was conducted in a Canadian Council on Animal Care approved facility in accordance with the CCAC Guide for Care and Use of Experimental Animals. Animals were spinalized 7 days prior to testing. A complete transection of the spinal cord was performed intervertebrally between the $9^{th}$ and $10^{th}$ vertebrae in isoflurane (2.5%) anesthetized animals. Complete spinalization was confirmed by 1) full paralysis of the hindlimbs, 2) post-mortem examination of the spinal cord microscopically and, in some cases, 3) staining transverse or sagittal spinal cord sections with luxol fast blue/cresyl violet for myelinated axons and nissl substance respectively. All mice received pre-operative care and post-operative care including lactate-Ringer's solution (2 ml/day, s.c.), analgesic (buprenorphine 0.2 mg/kg/day, s.c.) and antibiotic (baytril mg/kg/day, s.c.). Bladders were emptied manually and animals were left in their cage without other interventions with food and water ad libitum until testing. Mice received a single injection (i.p.) of 30-100 mg/kg L-DOPA (Sigma-Aldrich) one week post-spinalization. L-DOPA was used in combination with a peripheral decarboxylase inhibitor, benserazide (1:4) and, in some cases, with a monoamine oxydase inhibitor, nialamide (10 mg/kg, i.p.), in order to increase the central availability of L-DOPA.

Hindlimb movement recording, Hindlimb movements were filmed (digital video camera 3 Com Home-connect, 30 frames/sec) immediately prior to injection and at fixed delays after injection in animals suspended (air-stepping condition) or placed on a treadmill running at a speed of 8-10 cm/sec (treadmill condition). A harness was put around the torso and the waist either to completely suspend animals (air-stepping) or to maintain them in front of the camera on the treadmill (not weight support was provided). Animals were not stimulated otherwise.

Statistical analyses. Paired Student's t tests or one-way ANOVA were performed.

Results

Figure 4:
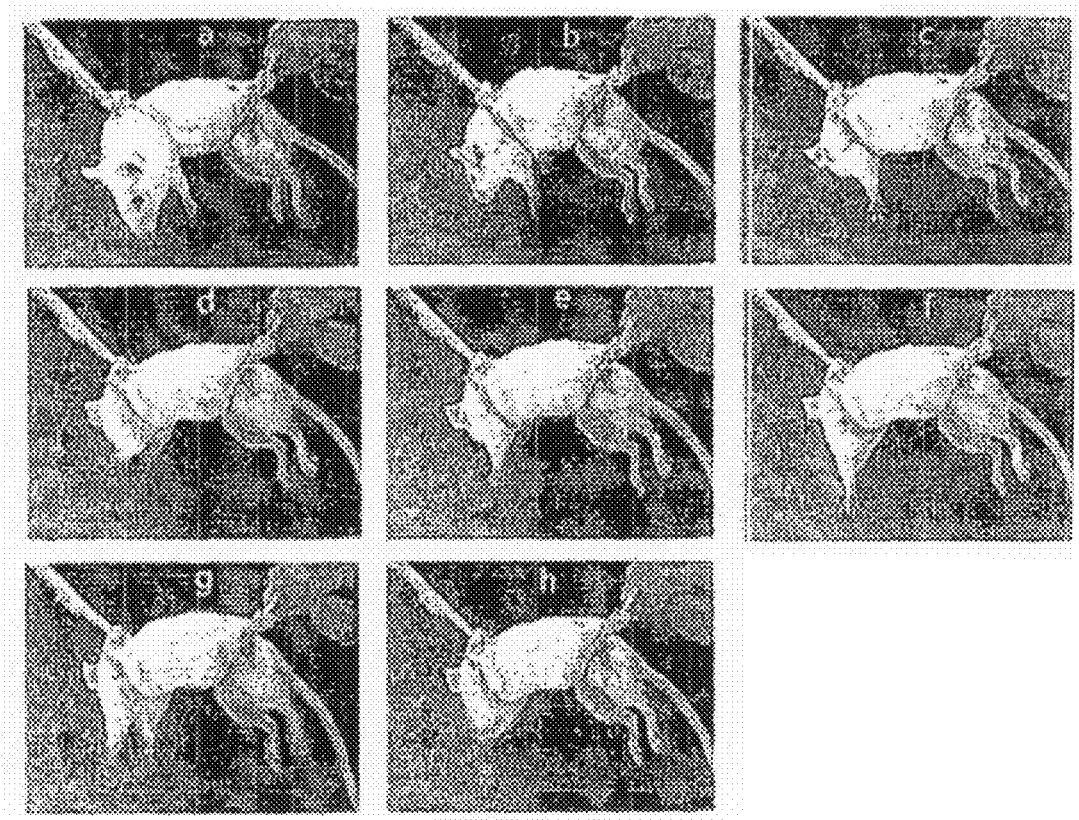
FIG. 4. Lack of effect of L-DOPA on hindlimb movement generation in the air-stepping condition. This 1-week paraplegic mouse received 40 mg/kg L-DOPA. No hindlimb movements were found 20 min post-injection (no effect either 30 or 45 min later). 0.5 sec between frames.
Figure 5:
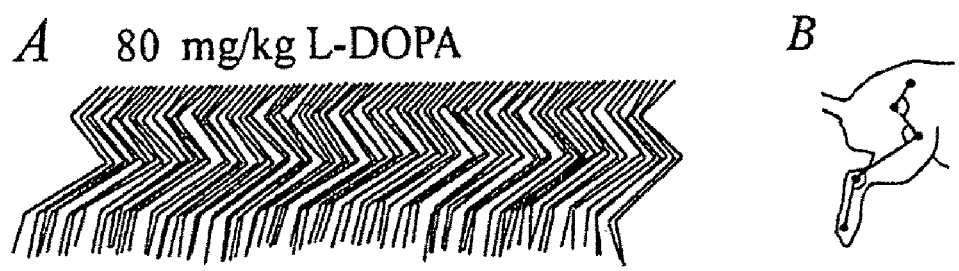
FIG. 5. Lack of effect of high doses of L-DOPA on hindlimb movement generation in the air-stepping condition. A. No movements 28 min after injection of 80 mg/kg L-DOPA. B. Stick diagram representation of the left hindlimb with the hip, knee and ankle joints represented. Mirror-images are shown for graphical purposes.
Figure 6:
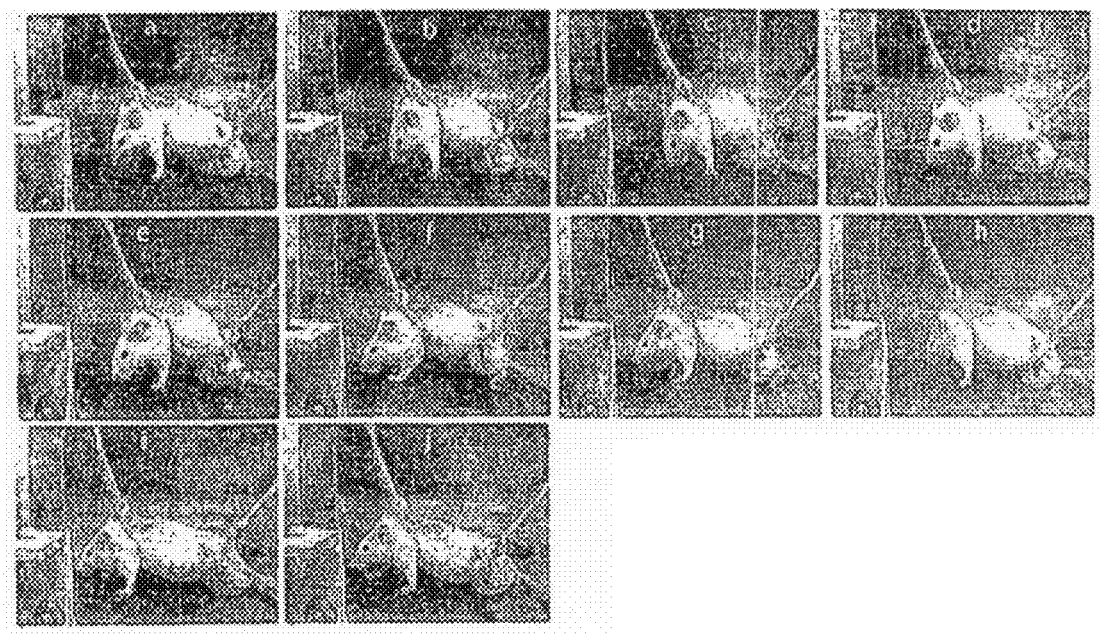
FIG. 6. Typical effect of 40 mg/kg L-DOPA in early chronic paraplegic mice placed on a motor driven treadmill. Same mouse as in FIGS. 4 and 5. After testing in air-stepping, the mouse placed on a treadmill running at 8 cm/sec displayed a combination of bilaterally alternating (or locomotor-like movements) and of non-bilaterally alternating (non-locomotor movements)
Figure 7:
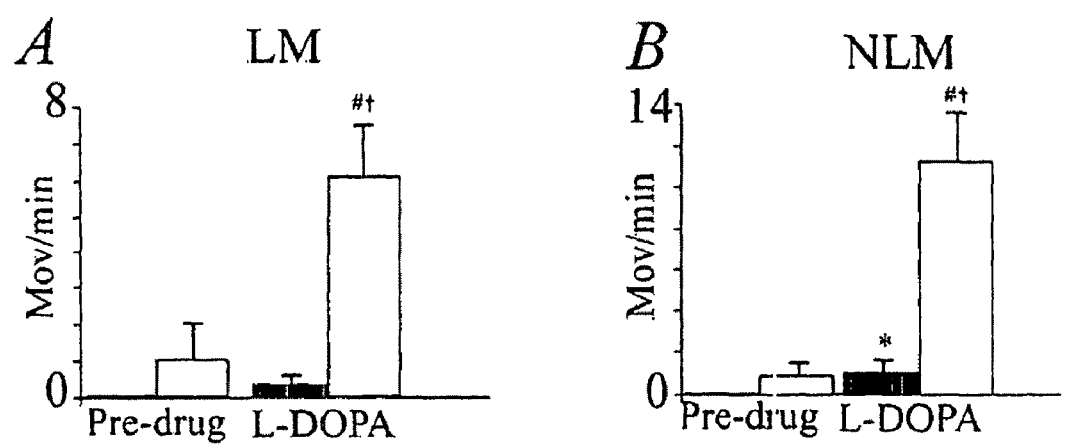
FIG. 7. Comparisons between L-DOPA-treatment (40-100 mg/kg) mice in air stepping (solid bars) vs. treadmill conditions (open bars). Pre-drug administration, no locomotor-like (stepping) movements were found in air-stepping. In contrast, placed on the treadmill, mice displayed a mixture of bilaterally alternating flexion-extension movements (6.1±1.3 LM) and of non-locomotor movements (11.2±1.8 NLM). n=29.

It was found that L-DOPA did not induce hindlimb movements in the air-stepping condition in these early chronic animals. Similar lack of effect was found in most mice tested although in few cases small amplitude non-locomotor movements (NLM) were found occasionally (see FIG. 7B, solid bar NLM). This is illustrated in FIG. 4 where no effects were displayed with 40 mg/kg L-DOPA. In another animal, no movements either were induced with relatively high doses of L-DOPA (80 mg/kg). This is illustrated with a stick diagram representation of the left hindlimb 20-30 min post-injection (FIG. 5). In contrast, doses >40 mg/kg L-DOPA (<40 mg/kg was uneffective) induced a mixture of locomotor-like movements (LM) and NLM on a motor-driven treadmill running (speed of 8-10 cm/sec). This is shown in FIG. 6 with a typical example where this mouse displayed hindlimb movements beginning 20 min following an injection of 40 mg/kg L-DOPA (same mouse as in FIG. 4). Data analyses shows that on average 6.1±1.3 LM and 11.2±1.8 NLM per min were induced by L-DOPA (40-100 mg/kg) on a treadmill (see FIGS. 7A and 7B respectively, open bars). It is important to mention that none of these movements supported the development of real locomotor movements. Hindlimbs remained, indeed in all cases, dragging behind with no weight bearing locomotor capabilities on the treadmill. Only small amplitude flexions and extensions alternating bilaterally resembling to crawling and therefore qualified as 'locomotor-like' in this study were induced by L-DOPA.

Conclusion

The results showed that L-DOPA can induce some movements on a treadmill with doses as low as 40 mg/kg but not in suspended animals (air-stepping). The induced movements were characterized by a combination of bilaterally alternating flexion-extension movements (locomotor-like or LM) and of non-locomotor movements (NLM or non-bilaterally alternating such as jerks, spasms, kicks, etc.). Movements induced by L-DOPA resembled more to sweeping than to walking given limited effects on restoring weight-bearing capabilities and proper plantar foot placement. L-DOPA used individually (i.e. not mixed with the serotonergic and dopaminergic agonists) was qualified therefore as being a mild activator of the lumbar spinal cord circuitry for hindlimb locomotion in paraplegic mice.

Example 3

Effects Induced by Various Subclasses of Serotonin Receptor Agonists Used Individually on the Induction of Leg Movements in Spinal Cord Injured Mice Materials and Methods Animals and Treatment. We tested one hundred and ninety five (n=195) male and female adult CD1 and C57BL/6 mice weighing 30-40 grams prior to the study (Charles River Laboratory, St-Constant, Canada). The experiment was conducted in a Canadian Council on Animal Care approved facility in accordance with the CCAC Guide for Care and Use of Experimental Animals. Animals were spinalized 7 days prior to testing (exceptionally tested sometimes at 15 days post-spinalization, e.g., FIG. 17). A complete transection of the spinal cord was performed intervertebrally between the $9^{th}$ and $10^{th}$ vertebrae in isoflurane (2.5%) anesthetized animals. Complete spinalization was confirmed by 1) full paralysis of the hindlimbs, 2) post-mortem examination of the spinal cord microscopically and, in some cases, 3) staining transverse or sagittal spinal cord sections with luxol fast blue/cresyl violet for myelinated axons and nissl substance respectively. All mice received pre-operative care and post-operative care including lactate-Ringer's solution (2 ml/day, s.c.), analgesic (buprenorphine 0.2 mg/kg/day, s.c.) and antibiotic (baytril 5 mg/kg/day, s.c.). Bladders were emptied manually and animals were left in their cage without other interventions with food and water ad libitum until testing. Mice received a single injection (i.p.) of either 8-OHDPAT (5-HT1A/7); 5-CT (5-HT1A/7 agonist); buspirone (5-HT1A agonist); TFMPP (5-HT1B/2C agonist); quipazine (5-HT2B/2C); m-CPP (5-HT2B/2C agonist); SR-57227A (5-HT3) one week post-spinalization. To dissect the contribution of 5-HT1A and 5-HT7 receptors, some of the mice were pretreated with highly selective antagonists such as WAY100,135 (5-HT1A antagonist), WAY100,635 (5-HT1A antagonist) or SB269970 (5-HT7 antagonist). The contribution of spinal 5-HT4/5/6 receptor activation to hindlimb movement generation in spinalized animals were not tested either because selective ligands are not available or because no significant expression levels have been found for these receptor subtypes in the mammalian spinal cord (see Schmidt and Jordan, *Brain Res Bull* 2000).

Hindlimb movement recording. Hindlimb movements were filmed (digital video camera 3 Com Home-connect, 30 frames/sec) immediately prior to injection and at fixed delays after injection in animals either suspended (air-stepping condition) or placed on a treadmill running at a speed of 8-10 cm/sec (treadmill condition). A harness was put around the torso and the waist either to completely suspend animals (air-stepping) or to maintain them in front of the camera on the treadmill (not weight support was provided). Animals were not stimulated otherwise. Locomotor-like movements were defined as rhythmic flexions and extensions occurring in both hindlimbs alternatively. Body weight support and plantar foot placement were facultative and therefore not required to be counted as locomotor-like (LM). In turn, non-locomotor movements (NLM) were defined as non-bilaterally alternating hindlimb movements most often including spasms, kicks, uncoordinated or unilateral movements, etc. In some cases, qualitative assessment methods were used to evaluate the level of induced hindlimb movements. The BBB locomotor scale (Basso, Bresnahan and Beattie, *Exp Neurol* 1996) and the AOB motor scale (Antri, Orsal and Barthe, *Eur J Neurosci* 2002) were also occasionally used.

Statistical analyses. Paired Student's t tests or one-way ANOVA were performed.

Results

Figure 8:
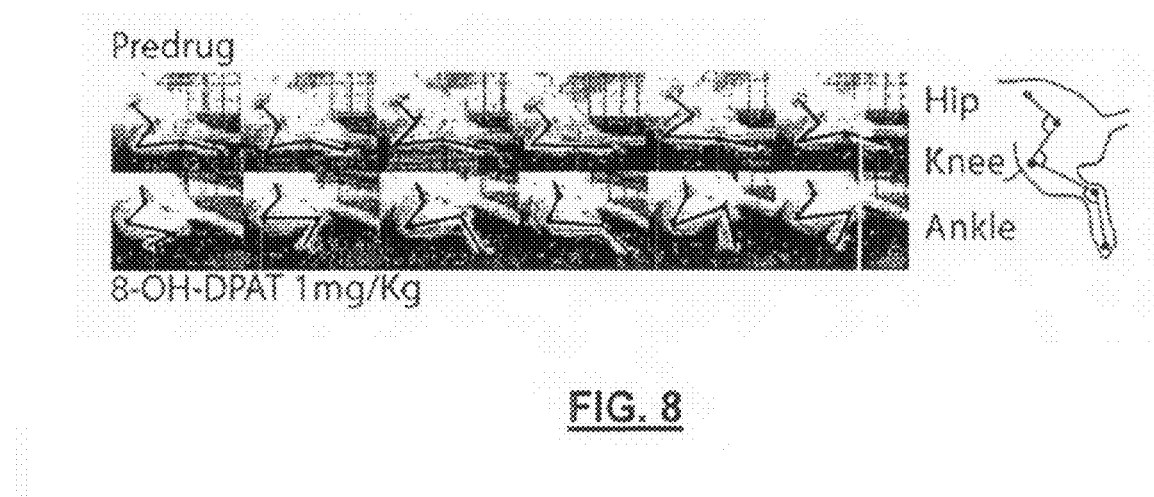
FIG. 8. Effect of 8-OH-DPAT in a paraplegic mouse. Pre-drug: a typical example illustrating the lack of hindlimb movement prior to drug administration. 8-OH-DPAT: 15 min after drug administration, flexions followed by extensions are regularly displayed. Note that no weight supported movements nor plantar foot placements were found.

5-HT1A and 5-HT7 receptor agonists We subjected two strains (CD1 and C57Bl/6) of male adult paraplegic mice to 8-hydroxy-2-(di-n-propylamino)tetralin (8-OH-DPAT), a highly potent and centrally active $5\text{-HT}_{1A}$ and $5\text{-HT}_7$ agonist. Our experimental data suggest that 8-OH-DPAT (1 mg/kg, i.p.) induced hindlimb alternated movements in most mice, seven days after the transection. Some of these movements were characterized as LM although weight supported steps or plantar foot placements were not found (see FIG. 8). Blockade of 5-HT1A receptor (Ways; 100,135[2 mg/kg, i.p.] and 100,635[2 mg/kg, i.p.]) significantly reduced the 8-OH-DPAT-induced LM in both strains (FIG. 10). Similar results were found with a 5-HT$_7$ antagonist (SB269970 [2-15 mg/kg, i.p.]) prior to the administration of 8-OH-DPAT (FIG. 11). Nearly complete prevention of 8-OH-DPAT-induced LM was obtained in mice were that received a combination of both SB269970 and WAY 100,635 (2 mg/kg each one) (FIG. 12) simultaneously. Similar levels of NLM were also induced by 8-OH-DPAT (not shown). Doses <0.5 mg/kg were considered as subthreshold (see FIG. 18).

Complementary experiments were performed with other agonists of that same class. We tested a 5-HT1A agonist named buspirone hydrochloride (commercially available as Buspar@). In 5/7 spinal CD1 mice, 6-8 mg/kg i.p. buspirone hydrochloride induced a combination of LM and NLM in the previously immobile hindlimbs. Generally, these movements were not accompanied with significant body weight or plantar foot placement. Doses ≦4 mg/kg were subthreshold for LM generation (FIG. 17).

5-HT1B/2C agonist TFMPP, a 5-HT1B/2C agonist, was found not to induce LM in paraplegic mice. This is shown in FIG. 13 where increasing doses of TFMPP induced only NLM but no LM (FIG. 13B).

5-HT2B/2C agonist: m-CPP, a 5-HT2B/2C agonist, was found also not to induce LM in paraplegic mice. Similar results as described for TFMPP are shown in FIG. 13A.

Figure 9:
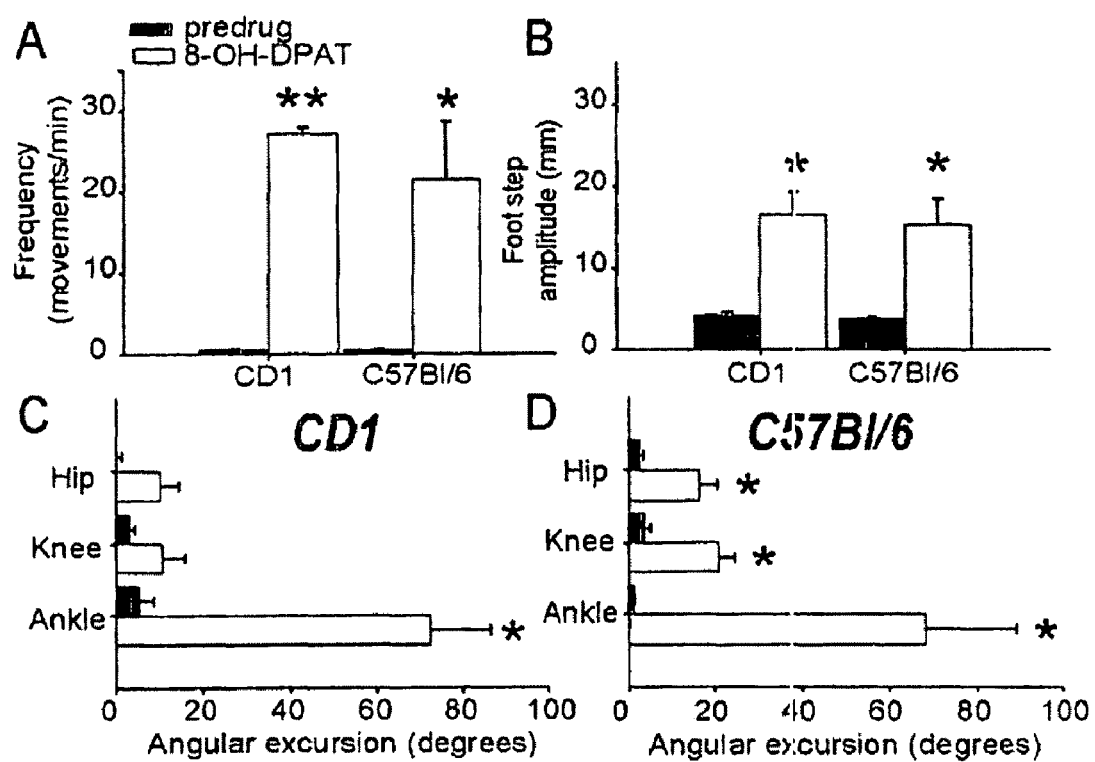
FIG. 9. Average effect induced by 8-OH-DPAT on hindlimb movement generation (n=40 paraplegic mice). A. Similar levels of locomotor-like movements were found in CD1 and C57Bl/6 mice. B. Movement amplitudes were also similar. C-D. Mostly angular excursion changes at the ankle joint level were found.

5-HT2B/2C agonist: In contrast to the results obtained with m-CPP and TFMPP, administration of quipazine induced some LM. This is shown in FIG. 14 where doses of quipazine above 0.8 mg/kg induced some rhythmic LM in air-stepping condition. Angular excursion changes mostly at the ankle and knee were found. On a treadmill as well as in air-stepping, quipazine induced LM as well as NLM. This is shown in FIG. 15, where 8-15 movements of each type of movements were reported. This is approximately 2-3 times less LM than 8-OH-DPAT tested in similar conditions (see FIG. 9 vs. FIG. 15).

5-HT3 agonist We found that the highly selective 5-HT3 receptor agonist, SR-57227A, can induce only NLM in the hindlimbs of paraplegic mice. This is shown in FIG. 16 where very low scores were found with the BBB and Antri motor scales. More analyses revealed that most of these movements corresponded to NLM. Only few LM were found occasionally on a running treadmill.

Conclusion

The results showed that among a wide variety of subclasses of 5-HT receptor agonists used individually, 8-OH-DPAT (5-HT1A/7 agonist) and buspirone (5-HT1A agonist) and to a lesser extent quipazine (5-HT2B/2C agonist), induced locomotor-like movements (LM) in complete paraplegic mice. The concomitant use of selective antagonists revealed that both 5-HT1A and 5-HT7 receptors participated in mediating the effects induced by 8-OH-DPAT.

TFMPP (5-HT1B/2C agonist), m-CPP (5-HT2B/2C agonist) or SR-57227A (5-HT3 agonist) induced NLM only. Altogether, these results strongly suggest that 5-HT1A, 5-HT7 and to some extend, 5-HT2B/2C, are the best subclasses of 5-HT agonists for inducing hindlimb locomotor-like movements in paraplegic animals. They could therefore qualify as mild activators of the lumbar spinal cord circuitry for hindlimb locomotion in paraplegic mice.

Example 4

Effects Induced by Various Subclasses of Dopamine Receptor Agonists Used Individually on the Induction of Leg Movements in Spinal Cord Injured Mice Materials and Methods Animals and Treatment. We tested forty-nine (7 animals/group×7 groups) male and female adult CD1 mice weighing 30-40 grams prior to the study (Charles River Laboratory, St-Constant, Canada). The experiment was conducted in a Canadian Council on Animal Care approved facility in accordance with the CCAC Guide for Care and Use of Experimental Animals. Animals were spinalized 7 days prior to testing. A complete transection of the spinal cord was performed intervertebrally between the $9^{th}$ and $10^{th}$ vertebrae in isoflurane (2.5%) anesthetized animals. Complete spinalization was confirmed by 1) full paralysis of the hindlimbs, 2) postmortem examination of the spinal cord microscopically and, in some cases, 3) staining transverse or sagittal spinal cord sections with luxol fast blue/cresyl violet for myelinated axons and nissl substance respectively. All mice received pre-operative care and post-operative care including lactate-Ringer's solution (2 ml/day, s.c.), analgesic (buprenorphine 0.2 mg/kg/day, s.c.) and antibiotic (baytril 5 mg/kg/day, s.c.). Bladders were emptied manually and animals were left in their cage without other interventions with food and water ad libitum until testing. Mice received a single injection (0.5-2.5 mg/kg, i.p.) of either SKF-81297 (D1/D5 agonist); A-68930 (D1-like agonist); apomorphine (D1/D2 agonist); quinpirole (D2/D3 agonist); 7-OH-DPAT (preferential D3 agonist); PD168077 (D4 agonist) 6-7 days post-spinalization. To dissect the contribution of D1 and D5 receptors, some of the mice tested with SKF-81297 were pretreated with a highly selective D1 antagonist SCH23390.

Hindlimb movement recording. Hindlimb movements were filmed (digital video camera 3 Com Home-connect, 30 frames/sec), 1) immediately prior to injection and, 2) at fixed delays after injection in animals placed on a treadmill running at a speed of 8-10 cm/sec (treadmill condition). A harness was put around the torso and the waist to maintain them in front of the camera on the treadmill (not weight support was provided). Animals were not stimulated otherwise. Hindlimb movements were assessed either as locomotor-like movements (LM) or non-locomotor movements (NLM) and expressed as single averaged combined scores (ACOS) calculated as follows: ACOS=(NLM+[LM×2]). For details, see an article by Guertin P. A. published in Spinal Cord (2005, no. 43, page 162-166). Locomotor-like movements were defined as rhythmic flexions and extensions occurring in both hindlimbs alternatively. Body weight support and plantar foot placement were facultative and therefore not required to be counted as locomotor-like (LM). In turn, non-locomotor movements (NLM) were defined as non-bilaterally alternating hindlimb movements most often including spasms, kicks, uncoordinated or unilateral movements, etc.

Statistical analyses. Paired Student's t tests or one-way ANOVA were performed.

Results

D1/D5 receptor agonist: SKF-81297 (D1/D5 agonist) administration induced in 71% of the mice a mixture of LM and NLM (FIG. 19) corresponding to an ACOS >8 (FIG. 21). Administration of A-68930 ($D_1$-like agonist) or apomorphine (D1/D2 agonist) also induced LM and NLM in 28% and 11% of the mice tested respectively (FIG. 19). Quinpirole (D2/D3 agonist), 7-OH-DPAT (D3 agonist) and PD168077 (D4 agonist) did not induce LM although some NLM were found (FIG. 20) leading nonetheless to ACOS values between 0 and 1.5 (not shown). This suggests that that D2, D3 and D4 receptor subtypes are not involved in LM movement generation in paraplegic mice. Some mice were pretreated with SCH23390 15 prior to SKF 81297 administration to distinguish D1 from D5 receptor activating-induced effects on hindlimb movement generation. The D1 antagonist largely reduced the ACOS values induced by SKF 81297 suggesting that both D1 and D5 are involved in generating hindlimb movement in spinal animals (FIG. 21). None of these dopaminergic agonists induced hindlimb movements that were accompanied of body weight support and plantar foot placement. LM resembled therefore to rhythmical bilaterally alternating sweeping movements.

Conclusion

The results showed that among a wide variety of subclasses of dopamine receptor agonists used individually, only few agonists that display some affinity for the D1 and D5 receptors can induce locomotor-like movements in the hindlimbs of paraplegic mice. Therefore, only SKF 81297, A-68930, and apomorphine were found to induce some locomotor-like movements (LM). In contrast, D2, D3 and D4 agonists such as quinpirole, 7-OH-DPAT and PD168077 induced only some NLM. Therefore, D1 and D5 receptor agonists used individually can be qualified as mild activators of the lumbar spinal cord circuitry for hindlimb locomotion in paraplegic mice.

Example 5

Influence of Route of Administration, Benserazide, Gender, Specie and Time Post-Spinal Cord Injury on Treatment-Induced Leg Locomotor Movement Generation in Spinal Cord Injured Animals Introduction Throughout the entire drug testing process that has led to the present discovery, most experiments were performed using in a highly-standardized animal model to facilitate, validate and easily compare the effects induced by various drugs and drug combinations. Experiments were mainly performed therefore using intraperitoneal injections of drugs in adult mice (typically male CD1) that were spinal cord transected 6-9 days prior to testing.

As previously presented, we found that L-DOPA/benserazide combined with a serotonin receptor agonist and a dopamine receptor agonist can acutely induce "automatic" stepping movements for approximately one hour in the hindlimbs of completely spinal cord transected mice.

However, to extend these observations further, we wanted to test whether this treatment is effective also 1) when administered via other systemic routes of administration such as subcutaneously; 2) without benserazide, a non-centrally active drug used solely as a peripheral decarboxylase inhibitor to enhance the penetration and bioavailability of L-DOPA to the central nervous system- i.e. spinal cord; 3) in female as well as in male given that gender-specific differences may exist in some cases for other drugs; 4) in different species such as in turtles that would strengthen the idea that the treatment is likely effective in all vertebrate species from phylogenetically primitive species such as amphibians to most recent species such as mammals; 5) in animals that have been acutely (within a few hours to a few days) or chronically (several weeks) spinal cord injured to assessed whether the treatment would be useful in acute patients only or also in chronic SCI individuals.

Methods

We used mice and *pseudemys scripta* turtles for these experiments. The experiment was conducted in a Canadian Council on Animal Care approved facility in accordance with the CCAC Guide for Care and Use of Experimental Animals. For surgical and other methodological procedures (e.g. hindlimb movement recording), see previous Examples.

L-DOPA/(with or without benserazide)+a serotonin receptor agonist+a dopamine agonist were injected in spinal cord transected animals. The effects of injections performed either intraperitoneally or subcutaneously were examined. The effects in female and male mice (CD1 strain) were also assessed. Effects were tested in mice or turtles (pseudemys scripta) at different time points post-injury (at 1, 7, 14 and 21 days post-spinal cord transection).

Results

Effects induced with subcutaneous administration. We tested the effects of 45 mg/kg L-DOPA/benserazide (10 mg/kg)+buspirone (1.5 mg/kg)+apomorphine (1.5 mg/kg) injected subcutaneously rather than intraperitoneally (for intraperitoneal injection-induced effects, see Example 1, FIG. 1). In 5/6 paraplegic mice tested (7 or 14 days post-spinalization), subcutaneous administration of the treatment induced hindlimb locomotor movements (15.4±3.2 LM per min) that displayed occasional-to-frequent weight-bearing support and plantar foot placement.

Effects induced with per os administration. Four (4) CD1 male mice spinalized 14 days before testing were used for this study. Administration of L-DOPA (40-60 mg/kg)/benserazide (10-12 mg/kg)+apomorphine (1-2 mg/kg)+buspirone (1-2 mg/kg) with a thin flexible plastic tube inserted in the throat (forced-feeding) induced rhythmic hindlimb movements some of which were locomotor-like accompanied with some weight-bearing capabilities. However, only rare plantar foot placement were observed. These effects were found in 2/4 mice tested.

These results showed that p.o. administration is another method of administration by which this treatment can be successfully administered. The apparent less effectiveness observed (only 2/4 animals, and rare plantar foot placement) is most likely due to the fact that the same doses tested in i.p. and s.c. were used as well for p.o. It is generally accepted that p.o. administration lead to reduced central (CNS) availability unless higher doses are administered because of some degradation by gastric acids and by the liver.

Effects induced without benserazide. We found in five (5) paraplegic mice (male CD1) that benserazide is not absolutely required as part of the treatment to induce hindlimb stepping movements. Injections were performed intraperitoneally in mice spinal cord transected seven days prior to testing. In all cases, a single injection of L-DOPA (without benserazide)+buspirone+apomorphine induced some hindlimb stepping movements. However, higher doses of L-DOPA were required (60-65 mg/kg rather than 40 mg/kg) to induce these movements most probably in order to compensate for the increased peripheral decarboxylation levels of L-DOPA in absence of a peripherally active decarboxylase inhibitor such as benserazide. Also, less locomotor movements (LM) were found if compared with results presented previously using benserazide (see Example 1). We found indeed 5.4 LM and 10.8 NLM per min (n=5 mice) with the treatment without benserazide.

Although not systematically analyzed, weight-bearing steps and adequate plantar foot placement were not as frequently displayed as found with the treatment that included benserazide (see results from Example 1).

Effects in female. Some of these results were reported already (see Example 1). We found in 4/5 female mice spinal cord transected 7-8 days prior to testing that 40-50 mg/kg L-DOPA/benserazide (10-12 mg/kg)+8-OH-DPAT (1-2 mg/kg)+Apomorphine (1-2 mg/kg) steadily induced locomotor movements (average frequency of 18.2±4.2 LM per min) including occasional-to-frequent weight-bearing stepping and plantar foot placement. These results are entirely comparable to what was found in male (see Example 5). Similar effects were found also in female mice tested at other time points post-spinalization (see below Effects in animals tested at different time points post-spinal cord injury).

Effects in pseudemis scripta turtles. Two out of three (2/3) adult turtles spinalized one day prior to testing were found to generate rhythmic hindlimb movements following administration of the treatment (1 mg/kg 8-OH-DPAT+1 mg/kg apomorphine+40-50 mg/kg L-DOPA (benserazide 10-12 mg/kg). FIG. 22A shows the lack of movements in the hindlimbs of a turtle spinalized one day earlier. Drug administration (i.p.) induced within 15-20 min hindlimb movements with either bilateral synchronicity (swimming) or bilateral alternation (terrestrial walking, not shown). Indeed, this specie routinely uses both types of movements for locomotion.

Effects in animals tested at different time point post-spinal cord injury. Some of these results were reported previously (see Example 1). We found in mice spinalized at 14 or 21 days prior to testing similar results as in mice spinalized only 6-9 days prior to testing. Similar results were also found in animals spinalized only 1-3 hours prior to testing (see Effects in turtles). In 2/2 mice (female CD1), spinal cord transected 14 days prior to testing, administration of 60 mg/kg L-DOPA/benserazide (15 mg/kg)+buspirone (3 mg/kg)+apomorphine (3 mg/kg) induced locomotor movements with occasional-to-frequent weight-supported stepping and plantar foot placement. The induced-locomotor movements displayed an average frequency of 14.8±3.7 LM per min which is comparable to what was found in mice spinal cord transected at 6-7 days prior to testing (see Example 1). Similar results were found in 1 out of 2 mice spinal cord transected at 21 days prior to testing (average stepping frequency of 33 LM per min).

Conclusion

The treatment composed of L-DOPA, a serotonin receptor agonist, and a dopamine receptor agonist has been found to induce stepping movements even if benserazide is not present. The treatment induced comparable locomotor movements in the hindlimbs of paraplegic turtles or mice. No clear differences were found in male or female mice. Finally, comparable effects were found whether the treatment was injected in animals spinal cord transected at 1, 2, 7, 14 or 21 days prior to testing. Therefore, these results strongly suggest that this treatment can acutely induce automatically stepping movements with occasional-to-frequent body weight-bearing capabilities and plantar foot placement in vertebrate species from amphibians to mammals acutely or chronically spinal cord transected. Although, benserazide should preferably be used to allow better central bioavailability of L-DOPA, comparable effects with higher doses of L-DOPA can be found.

Example 6

Effects Induced by Combining Two Compounds Rather than all Three Centrally Active Families of Compounds on Leg Locomotor Movement Generation in Spinal Cord Injured Mice Methods We used adult CD1 mice spinal cord transected 8 days prior to testing. The experiment was conducted in a Canadian Council on Animal Care approved facility in accordance with the CCAC Guide for Care and Use of Experimental Animals. For surgical and other methodological procedures (e.g. hindlimb movement recording), see previous Examples.

L-DOPA/(benserazide) and/or a serotonin receptor agonist and/or a dopaminergic agonist were injected in spinal cord transected animals. The effects of injecting a combination comprising only two of these compounds were examined.

Results

Effects of L-DOPA/benserazide+Apomorphine. Four (n=4) female CD1 mice spinalized 8 days prior to testing were used for this series of experiments. We found in 3 out of 4 mice that 50 mg/kg L-DOPA/benserazide (12 mg/kg) co-administered with 2 mg/kg Apomorphine induced a mix of LM (13±5.1 per min) and NLM (20.5±3.2 per min). However, absolutely no body weight-bearing capabilities and plantar foot placement were observed.

Effects of 8-OH-DPAT+Apomorphine. Five (n=5) female CD1 mice spinalized 8 days prior to testing were used. We found in mice injected instead with 2-3 mg/kg 8-OH-DPAT and 2-3 mg/kg Apomorphine a mix of LM (32 per min, n=2/5) and NLM (5.75 per min, n=4/5) accompanied occasionally (in 2 out of 5 mice) only with partial weight-bearing stepping but with no plantar foot placement (i.e. dorsal foot placement).

Effects of L-DOPA/benserazide+8-OH-DPAT. Four (n=4) female CD1 mice spinalized 8 days earlier were tested. Injection of 40-50 mg/kg L-DOPA (benserazide 10-12 mg/kg)+1 mg/kg 8-OH-DPAT induced within 20 min substantially high LM frequency in 3/4 mice (29.0±9.1 per min) and moderate levels of NLM in 4/4 mice (7.2+2.3 per min). Occasional weight bearing stepping and only rare plantar foot placement were detected in 1/4 mice.

Effects of L-DOPA/benserazide+Buspirone. One (n=1) male CD1 mice spinalized 16 days prior to testing received 60 mg/kg L-DOPA/benserazide (15 mg/kg)+3 mg/kg buspirone. On average, 7 LM per min and 14 NLM per min were found 20 min post-injection. Movements were of rather large amplitude with some weight-bearing and plantar foot placement capabilities.

Conclusion

Administration of only two compounds (L-DOPA/benserazide and/or a serotonin receptor agonist, and/or a dopamine receptor agonist) can occasionally induce stepping movements in complete paraplegic animals. The effects are generally superior regarding NLM and LM frequencies compared with results obtained using any of these compound individually (see Examples 2-4). In few animals, some of these combinations can induce hindlimb LM accompanied of some weight-bearing and plantar foot placement capabilities.

Example 7

General Conclusion

The effects induced by combining one or two centrally active compounds, which may be of the same family, can mildly activate the lumbar spinal cord circuitry for hindlimb locomotion in a paraplegic animal (see Examples 2-4, 6). Preferably, all three proposed families of compounds including a dopamine/noradrenaline precursor, a serotonin receptor agonist, and a dopamine receptor agonist may be used to induce within 15 minutes hindlimb movements lasting for approximately one hour that are characterized generally by bilaterally alternated flexion-extensions (LM) with weight-bearing and plantar foot placement capabilities (see Examples 1 and 5).

Although, benserazide should preferably be used to allow better central bioavailability of L-DOPA (and lower doses of L-DOPA to be used), comparable effects were found with higher doses of L-DOPA (see Example 5). These effects are by far superior (synergistic actions) to those induced by using each compound individually (see Examples 2-4). Indeed, the movements induced by each compound individually resemble more to sweeping than to real locomotion since only a mixture of NLM and LM without weight-bearing capabilities (rear end is supported by powerful muscular contractions) and plantar foot placement were found supporting the idea of powerful synergistic actions by combining them all. Example 5 provides evidence suggesting that the treatment is capable of inducing comparable movements in the hindlimbs of two phylogenetically very different vertebrate species, namely in turtles and mice supporting the hypothesis that similar effects may be found in most other vertebrate species including humans. No clear differences were found in male or female animals. Comparable effects were found whether the treatment was injected subcutaneously or intraperitoneally (also p.o to some extent) in animals spinal cord transected at 1, 2, 7, 14 or 21 days prior to testing (see Example 5). All and all, these results strongly suggest that this centrally-active treatment upon systemic delivery can acutely induce automatic (involuntary) stepping movements with occasional-to-frequent body weight-bearing and plantar foot placement capabilities in vertebrate species from amphibians to mammals acutely or chronically spinal cord transected. The proposed treatment can therefore temporarily restore functional and useful levels of locomotor recovery in spinal cord injured animals. Given that other neuropathological problems involved impaired locomotor function, this discovery may potentially be used also for patients with multiple sclerosis (MS), amyotrophic lateral sclerosis (ALS), cerebro-vascular diseases or trauma and other neurological disorders.

The invention claimed is:

1. A composition for inducing or restoring locomotor functions in an animal, said composition comprising:
   a) at least one dopamine receptor agonist, L-DOPA, and at least one 5-$HT_{1A}$ serotonin receptor agonist; or
   b) L-DOPA and at least one 5-$HT_{1A}$ serotonin receptor agonist,
wherein said locomotor functions being defined as rather well-coordinated and self-sustained weight bearing walking movements.

2. The composition according to claim 1, wherein said animal is a spinal cord injured animal.

3. The composition according to claim 1, wherein said dopamine receptor agonist is selected from the group consisting of apomorphine, ropinirole, pramipexole, pergoline, cabergoline, SKF81297, and combinations thereof.

4. The composition according to claim 3, wherein said dopamine receptor agonist is apomorphine.

5. The composition according to claim 1, further comprising a peripheral decarboxylase inhibitor.

6. The composition according to claim 5, wherein said peripheral decarboxylase inhibitor is benserazide.

7. The composition according to claim 1, wherein said 5-$HT_{1A}$ serotonin receptor agonist is selected from the group consisting of buspirone, 8-OH-DPAT, 5-CT, metergoline and pimozide.

8. The composition according to claim 7, wherein said serotonin receptor agonist is 8-OH-DPAT.

9. The composition according to claim 7, wherein said serotonin receptor agonist is buspirone.

10. A method for inducing or restoring locomotor functions in an animal, the method comprising the step of administering a therapeutically effective amount of a composition as defined in claim 1, wherein said locomotor functions being defined as rather well-coordinated and self-sustained weight bearing walking movements.

11. The method of claim 10, wherein the composition is administered in an amount ranging:
   from about 0.1 to about 1 mg/kg of dopamine receptor agonist;
   from about 5 to about 50 mg/kg of L-DOPA; and
   from about 0.1 to about 1 mg/kg of 5$HT_{1A}$ serotonin receptor agonist.

* * * * *